(12) United States Patent
Lewis et al.

(10) Patent No.: US 7,963,767 B2
(45) Date of Patent: Jun. 21, 2011

(54) SELF-LIGATING ORTHODONTIC BRACKET WITH SLIDING LIGATION COVER

(75) Inventors: Paul Lewis, Midvale, UT (US); Eldon Montgomery, Salt Lake City, UT (US)

(73) Assignee: Ultradent Products, Inc., South Jordan, UT (US)

( * ) Notice: Subject to any disclaimer, the term of this patent is extended or adjusted under 35 U.S.C. 154(b) by 295 days.

(21) Appl. No.: 12/146,608

(22) Filed: Jun. 26, 2008

(65) Prior Publication Data

US 2009/0325120 A1     Dec. 31, 2009

Related U.S. Application Data

(60) Provisional application No. 61/190,056, filed on Jul. 23, 2007.

(51) Int. Cl.
*A61C 3/00* (2006.01)
(52) U.S. Cl. ............................................. 433/10; 433/11
(58) Field of Classification Search .................. 433/8–11
See application file for complete search history.

(56) References Cited

U.S. PATENT DOCUMENTS

| | | |
|---|---|---|
| 2,011,575 A | 8/1935 | Ford |
| 2,549,528 A | 4/1951 | Russell |
| 3,578,744 A | 5/1971 | Wildman |
| 4,077,126 A | 3/1978 | Pletcher |
| 4,103,423 A | 8/1978 | Kessel |
| 4,268,249 A | 5/1981 | Forster |
| 4,371,337 A | 2/1983 | Pletcher |
| 4,419,078 A | 12/1983 | Pletcher |
| 4,491,825 A | 1/1985 | Tuthill |
| 4,559,012 A | 12/1985 | Pletcher |
| 4,634,662 A | 1/1987 | Rosenberg |
| 4,655,708 A | 4/1987 | Fujita |
| 4,698,017 A | 10/1987 | Hanson |
| 4,712,999 A | 12/1987 | Rosenberg |
| 4,820,151 A | 4/1989 | Pospisil |
| 5,037,297 A | 8/1991 | Lerner |
| 5,094,614 A | 3/1992 | Wildman |
| 5,123,838 A | 6/1992 | Cannon |

(Continued)

FOREIGN PATENT DOCUMENTS

EP      1723927      11/2006

(Continued)

OTHER PUBLICATIONS

"Carrière SLB Bracket: The Ned Standard for Self-Ligation", ClassOne Orthodontics, 2008, Based on information and belief, available as early as Aug. 22, 2007; Website: http://www.classoneorthodontics.com/slb.aspx.

(Continued)

*Primary Examiner* — Ralph A Lewis
(74) *Attorney, Agent, or Firm* — Workman Nydegger

(57) ABSTRACT

Self-ligating orthodontic brackets include a bracket base, at least one arch wire slot formed in the bracket base adapted to receive an arch wire therein, and a ligation cover which is selectively slidable relative to the bracket base between an open non-ligating position relative to the slot and a closed, ligating position relative to the slot. The exterior labial surface of both the base and ligation cover comprise a compound two axis curvature so that substantially all of the exterior labial surface of both the bracket base and the ligation cover present a smooth, continuous exterior surface that is substantially free of sharp discontinuities and crevices.

30 Claims, 14 Drawing Sheets

U.S. PATENT DOCUMENTS

| | | |
|---|---|---|
| 5,248,257 A | 9/1993 | Cannon |
| 5,275,557 A | 1/1994 | Damon |
| 5,299,934 A | 4/1994 | Suyama |
| 5,322,435 A | 6/1994 | Pletcher |
| 5,429,500 A | 7/1995 | Damon |
| 5,439,378 A | 8/1995 | Damon |
| 5,466,151 A | 11/1995 | Damon |
| 5,474,446 A | 12/1995 | Wildman et al. |
| 5,613,850 A | 3/1997 | Wildman et al. |
| 5,618,176 A | 4/1997 | Andreiko et al. |
| 5,630,715 A | 5/1997 | Voudouris |
| 5,782,631 A | 7/1998 | Kesling et al. |
| 6,042,373 A | 3/2000 | Hermann |
| 6,071,118 A | 6/2000 | Damon |
| 6,071,119 A | 6/2000 | Christoff et al. |
| 6,190,166 B1 | 2/2001 | Sasakura |
| 6,193,508 B1 | 2/2001 | Georgakis |
| 6,206,690 B1 | 3/2001 | Vargas |
| 6,220,857 B1 | 4/2001 | Abels |
| 6,247,923 B1 | 6/2001 | Vashi |
| 6,347,939 B2 | 2/2002 | Abels |
| 6,695,612 B2 | 2/2004 | Abels et al. |
| 6,726,474 B2 | 4/2004 | Spencer |
| 6,776,613 B2 | 8/2004 | Orikasa |
| 6,843,651 B2 | 1/2005 | Orikasa |
| 6,866,505 B2 | 3/2005 | Senini |
| 6,964,565 B2 * | 11/2005 | Abels et al. ............ 433/10 |
| 7,025,591 B1 * | 4/2006 | Kesling ............ 433/10 |
| 7,033,170 B2 | 4/2006 | Cordato |
| 7,255,557 B2 | 8/2007 | Forster |
| 7,267,545 B2 | 9/2007 | Oda |
| 7,335,020 B2 * | 2/2008 | Castner et al. ............ 433/11 |
| 7,611,352 B2 * | 11/2009 | Abels et al. ............ 433/10 |
| 7,621,743 B2 * | 11/2009 | Bathen et al. ............ 433/10 |
| 7,704,072 B2 * | 4/2010 | Damon ............ 433/11 |
| 2004/0072117 A1 | 4/2004 | Farzin-Nia et al. |
| 2004/0157186 A1 | 8/2004 | Abels et al. |
| 2004/0158194 A1 | 8/2004 | Wolff et al. |
| 2005/0186525 A1 | 8/2005 | Abels et al. |
| 2005/0239012 A1 | 10/2005 | Bathen et al. |
| 2005/0244773 A1 | 11/2005 | Abels et al. |
| 2005/0244774 A1 | 11/2005 | Abels et al. |
| 2005/0255422 A1 | 11/2005 | Cordato |
| 2006/0003281 A1 | 1/2006 | Nicholson |
| 2006/0003282 A1 | 1/2006 | Nicholson |
| 2006/0024635 A1 | 2/2006 | Lai |
| 2006/0046223 A1 | 3/2006 | Abels et al. |
| 2006/0051721 A1 | 3/2006 | Carriere Lluch |
| 2006/0084025 A1 | 4/2006 | Abels et al. |
| 2006/0110699 A1 | 5/2006 | Forster |
| 2006/0147868 A1 | 7/2006 | Lai et al. |
| 2006/0154196 A1 | 7/2006 | Oda |
| 2006/0172248 A1 | 8/2006 | Sarnetz et al. |
| 2006/0228662 A1 | 10/2006 | Lokar et al. |
| 2006/0228664 A1 | 10/2006 | Castner et al. |
| 2007/0009849 A1 | 1/2007 | Wool |
| 2007/0082315 A1 | 4/2007 | Sabater |
| 2007/0160949 A1 | 7/2007 | Voudouris |
| 2008/0113311 A1 * | 5/2008 | Forster ............ 433/11 |

FOREIGN PATENT DOCUMENTS

| | | |
|---|---|---|
| ES | 2 204 333 | 4/2004 |
| ES | 2 208 114 | 6/2004 |
| ES | 2 209 599 | 6/2004 |
| WO | WO 99/40871 | 8/1999 |
| WO | WO 2004/047665 | 6/2004 |

OTHER PUBLICATIONS

Ormco Corporation, "Proven Performance form Start to Finish", Based on information and belief, available as early as Aug. 22, 2007; Website: http://www.ormco.com/index/damon.

"Axis Self-Ligating System", 2008 Ortho Classic, Based on information and belief, available as early as Aug. 22, 2007; Website: http://www.orthoclassic.com/slbbracketsystem.htm.

Ormco Orthodontic Products Catalog, Ormco Corporation, 2007, Based on information and belief, available as early as Aug. 22, 2007.

* cited by examiner

SELF-LIGATING ORTHODONTIC BRACKET WITH SLIDING LIGATION COVER

RELATED APPLICATIONS

The present application claims the benefit of U.S. Provisional Patent Application Ser. No. 61/190,056, filed Jul. 23, 2007, entitled "SELF LIGATING ORTHODONTIC BRACKET WITH SLIDING LIGATION COVER", the disclosure of which is incorporated by reference in its entirety.

BACKGROUND OF THE INVENTION

1. The Field of the Invention

The present invention relates to orthodontic brackets, more particularly to two-part self-ligating orthodontic brackets that include a bracket base, at least one slot for receiving an arch wire, and a ligating cover.

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth to correct overjets or overbites. For example, orthodontic treatment can improve the patient's occlusion, or enhanced spatial matching of corresponding teeth.

The most common form of orthodontic treatment involves the use of orthodontic brackets and wires, which together are commonly referred to as "braces." Orthodontic brackets, more particularly the orthodontic bases, are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the slot of each bracket. The arch wire acts as a template or track to guide movement of the teeth into proper alignment.

There are two distinct classes of orthodontic brackets: those that require the use of ligatures to fasten the arch wire to the bracket, and those that are self-ligating. In brackets of the first class, small ligature wires are typically used to hold the arch wire in a securely seated position in the brackets. Ligatures or some other form of fastening means are essential to ensure that the tensioned arch wire is properly positioned around the dental arch, and to prevent the wire from being dislodged from the bracket slots during chewing of food, brushing of teeth, or application of other forces. One type of commercially available ligature is a small, elastomeric O-ring, which is installed by stretching the O-ring around small wings known as "tie wings" that are connected to the bracket body. Metal ligatures are also used to retain arch wires within the bracket slots.

In an effort to simplify the process of installing braces, a variety of self-ligating brackets have been developed. The term "self-ligating bracket" refers to a class of orthodontic brackets that include some sort of cover, whether separate from, hingedly or otherwise attached to the base, which encloses or otherwise retains the arch wire within the slot of the base.

A typical orthodontic practitioner may see as many as 80 patients in a single day. As such, the amount of time that can be allocated to each patient may be quite limited. Self-ligating brackets are typically installed and adjusted much more quickly than brackets requiring the use of ligatures. As such, self-ligating brackets provide a distinct advantage in terms of decreasing the amount of time that must be spent with each patient. Although existing self-ligating brackets do provide ease of use and can be adjusted relatively quickly by the practitioner, it would be an improvement in the art to further reduce the amount of time required to make adjustments (e.g., open the bracket covers, insert and/or remove arch wires, and then close the bracket covers), allowing the practitioner to see additional patients within a working day and/or address other issues that the patient may have.

BRIEF SUMMARY OF THE PREFERRED EMBODIMENTS

Embodiments of the invention are directed to self-ligating orthodontic brackets which include a bracket base, at least one arch wire slot formed in the bracket base adapted to receive an arch wire therein, and a ligation cover which is selectively slidable relative to the bracket base between an open non-ligating position relative to the slot and a closed, ligating position relative to the slot. The exterior labial surface of the bracket (which is substantially all portions of the bracket visible during use) is advantageously smooth, continuous, and substantially free of crevices, discontinuities, or intricate structures.

The exterior labial surface of both the bracket base and the cover comprise a compound curvature which is curved in two axes (i.e., curved in two directions simultaneously). In other words, the labial exterior surface curves relative to a longitudinal as well as a latitudinal axis of the bracket. The exterior surface curvature is smooth and substantially continuous, thus minimizing or eliminating the presence of crevices, discontinuities, or intricate structures along this surface. Any included recess (e.g., a single recess in the cover and/or base to aid in opening the cover) is advantageously smoothly curved as well so as to eliminate the presence of sharp corners on the exterior labial surface of the bracket. Such a smooth and continuous surface is beneficial as it minimizes the tendency for food or other debris to become lodged on or attached to the bracket. It is particularly advantageous that the exposed labial surface of the bracket be substantially free of crevices and other intricate features, as accumulation of food or other debris, which would be easily visible on this surface, is minimized.

The orthodontic bracket is easily manufactured. For example, the bracket may consist of only two parts (i.e., a bracket base and a sliding ligation cover) that may be formed by casting, machining, injection molding, metal injection molding, or liquid metal injection molding. In order to further simplify manufacture, the bracket base and ligation cover may be configured to minimize the presence of intricate portions, which otherwise may require intricate machining work, or if molded, may often result in breakage of such small, intricate portions, resulting in increased waste.

According to one embodiment, the bracket further includes latch means for holding the ligation cover in an open position when open. Preferably, the bracket further includes latch means for holding the cover in a closed position when closed. The ability of the bracket to hold the cover open when in the open position is advantageous as it allows the orthodontic practitioner to more easily and quickly insert and/or remove the arch wire during a visit of the patient to the practitioner's office (i.e., the cover is less likely to close on its own under force of gravity or as a result of being bumped). In addition, the sliding connection between the ligation cover and the bracket base is advantageous as it is more robust and quicker to open and close as compared to rotating hinge type connections. Furthermore, the operation of hinge type connections is sometimes painful for the patient, as forces applied to open the bracket are transferred to the underlying tooth, whereas operation of the sliding mechanism of the present inventive bracket is more efficient in isolating applied forces from the underlying tooth, resulting in increased comfort for the patient during adjustments at the office of the orthodontic practitioner. As a further advantage, the latch mechanism which latches the cover open when open and/or closed when closed is configured and located so as to not be externally exposed, which helps prevent food and/or debris from becoming lodged therein.

The bracket base may advantageously be formed of metal, ceramic, or glass so as to provide high strength, which is helpful in the region of the arch wire slot as it aids in transferring forces from the arch wire to the bracket base so as to effect movement of the teeth without deformation of the material surrounding the slot. Metal, ceramic, and/or glass materials are particularly strong so as to resist deformation, and for this reason these materials are preferred for manufacturing the bracket base. It may also be possible to form the bracket base from a rigid and strong polymeric resin material, although metals, ceramics, and/or glass materials may be preferred for their increased resistance to deformation as compared to polymeric materials.

The ligation cover may advantageously be formed of metal, ceramic, glass, or a polymeric resin. In addition to different choice of material properties that such a two-part bracket provides (i.e., the cover may be of a different material than the bracket base), such a two-part bracket allows the patient and practitioner some flexibility in creating a desired aesthetic appearance to the bracket and the overall bracket system, as the ligation cover(s) may be of a different material (and/or color and/or texture) than the bracket base(s). For example, a bracket base may be of a first color, while the associated ligation cover is of a second different color. Many patients (typically those who are young) enjoy the aesthetic appearance provided by brackets exhibiting bright and/or high contrast, easily noticeable colors. In addition, the ligation cover and/or bracket base may include a decorative image, graphic, figure, pattern, design, or other decoration according to the aesthetic wishes of the patient.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

Embodiments of the present invention are directed to self-ligating orthodontic brackets that include a bracket base, at least one arch wire slot formed in the bracket base adapted to receive an arch wire therein, and a ligation cover which is selectively slidable relative to the bracket base between an open non-ligating position relative to the slot and a closed, ligating position relative to the slot. In addition, the exterior labial surface of both the base and ligation cover comprise a compound two axis curvature so that substantially all of the exterior labial surface (e.g., as seen from a "planar top" view of the bracket—similar to the view of the brackets by an observer of a patient wearing the brackets) of both the bracket base and the ligation cover present a smooth, continuous exterior surface that is substantially free of sharp discontinuities and crevices. Any included recess (e.g., a single small configured to aid in opening the ligation cover with a tool) is formed so as to minimize sharp angles, small discontinuities and crevices.

II. Exemplary Orthodontic Brackets

Figure 1A:
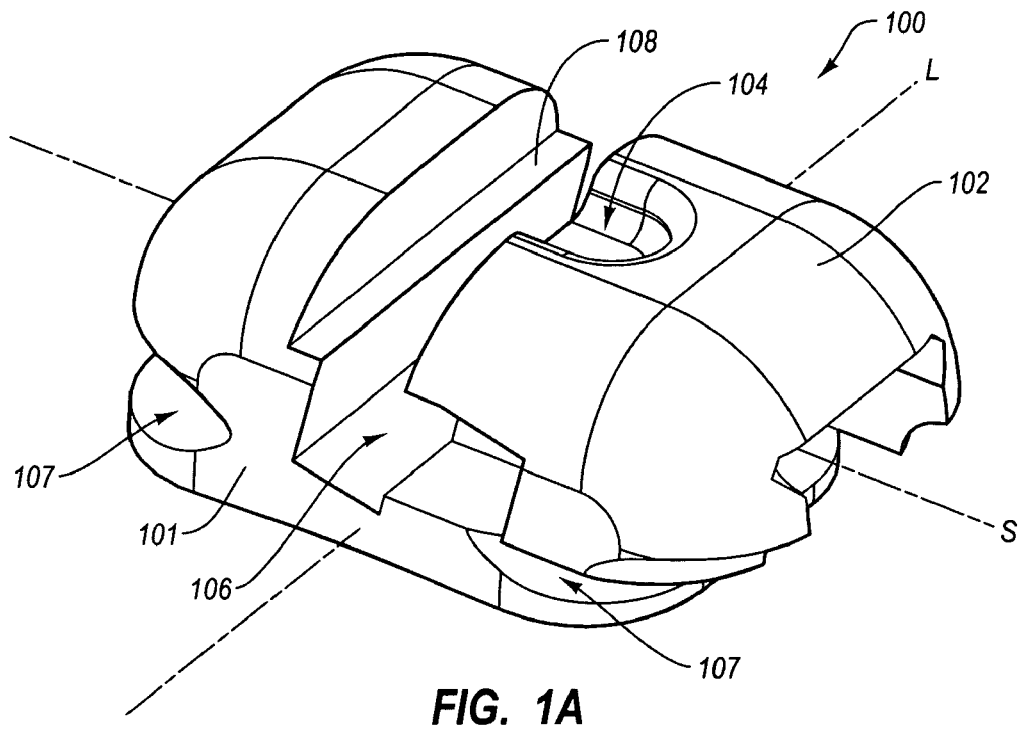
FIG. 1A is a perspective view of an exemplary orthodontic bracket according to the present invention shown in the open position.
Figure 1B:
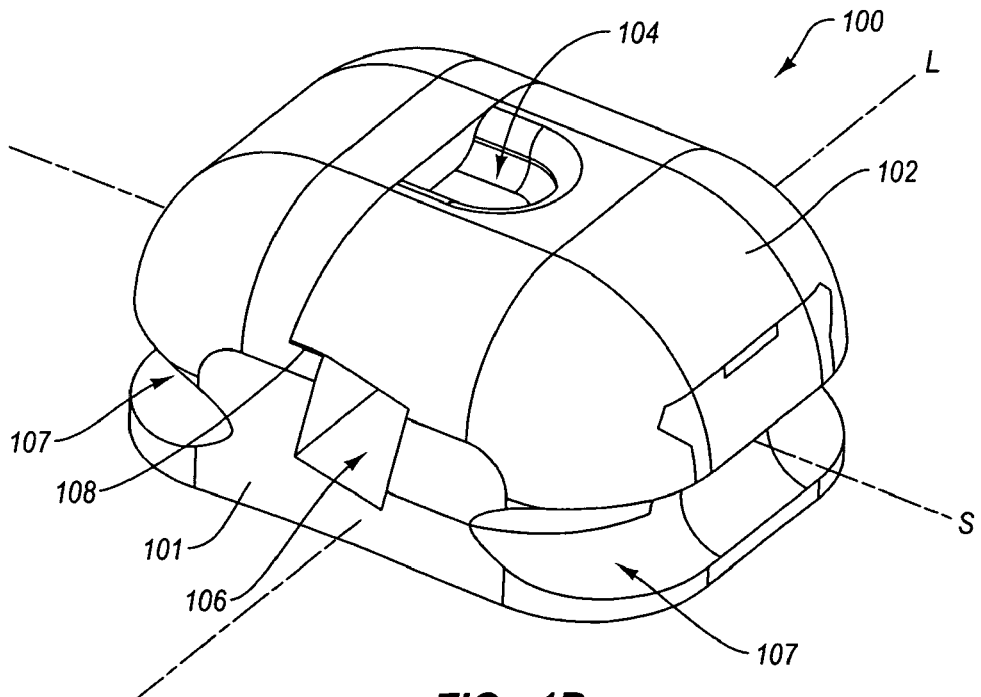
FIG. 1B is a perspective view of the orthodontic bracket of FIG. 1A with the ligation cover in an closed position relative to the bracket base.

FIGS. 1A-1B illustrate an exemplary orthodontic bracket 100. Bracket 100 includes a bracket base 101 and ligation cover 102. Once assembled, the base 101 and cover 102 are slidably connected to each other via a sliding joint mechanism defined by a sliding axis S along which ligation cover 102 can be slid from an open position as shown in FIG. 1A to a completely closed and latched position shown in FIG. 1B.

In the illustrated embodiment, ligation cover 102 includes a recess 104. In order to open cover 102 relative to slot 106, a tool (e.g., a dental scaler) may be inserted within recess 104. A force is applied with the scaler or other tool to pull cover 102 open. Recess 104 is advantageously relatively narrow so as to prevent or at least inhibit a patient from being able to unlock the cover of the bracket with his or her own fingernail. For example, the recess 104 may have a width between about 0.25 mm and about 1 mm, more preferably between about 0.5 mm and about 0.75 mm. In addition, recess 104 is illustrated as U shaped, which is consistent with the smooth, substantially crevice free configuration of the labial face of the bracket, and which also easily receives and guides a dental tool down towards the lowest portion of the U shaped recess so as to pull the cover open. A V shaped recess may alternatively be employed, although the smooth U shape is preferred as it further minimizes the presence of sharp angles on the labial face of the bracket in closed configuration.

Exemplary latch mechanisms configured to maintain the cover in an open position when open and closed when closed will be described in further detail below. Force applied to recess 104 must be sufficient to unlock the latch mechanism so as to allow the cover to slide open. In reverse, the practitioner's finger may be used to apply a force to the incisal edge of cover 102, forcing it closed. The ability to close cover 102 without the use of any special tool (i.e., only a finger is needed) is advantageous as it further reduces the time required for the practitioner to make necessary adjustments, including closing the cover 102.

Ligation cover 102 advantageously moves in a flat, planar sliding motion relative to the bracket base 101. This allows the force applied to slide cover 102 into the open position to be efficiently transferred, resulting in motion of the cover while minimizing force that is transferred to the underlying tooth to which the bracket base 101 is attached. Such a sliding configuration results in less applied force being received by the underlying tooth as compared to brackets in which the cover is hingedly connected to the bracket base and in which the cover rotates relative to the base. Pulling up or down on the hinged cover (so as to open it) typically results in transmission of force to the underlying tooth, which can result in discomfort and/or pain to the patient. When the action is taken in reverse to close the cover, it is also very difficult to minimize transmission of force to the underlying tooth, again resulting in discomfort and/or pain. According to one embodiment, the planar, sliding connection provides a mechanism in which the cover slides parallel to the longitudinal axis of the tooth. Providing a planar, sliding motion is also more comfortable than a sliding configuration in which the slide path is curved, as it is difficult in practice to prevent transmission of force to the underlying tooth when maneuvering a ligation cover that follows a curved sliding path. For this reason, it is preferred that the connection mechanism between the bracket base and ligation cover provide for a planar sliding motion and slide path.

In addition, the time required to slide the cover 102 open relative to slot 106 is less than the time typically required to rotate a hinged cover. Such differences are particularly advantageous when multiplied over many brackets and many patients. For example, a full set (e.g., about 20-28 brackets) of installed brackets including sliding covers as shown in FIGS. 1A and 1B may be opened or closed in about 30 seconds or less, typically about 20 seconds or less. Such increases in speed and ease of opening and closing may result in significant time savings for the orthodontic practitioner when multiplied over as many as 80 (or even more) patients per day.

In the illustrated example, the labial exterior surfaces (e.g., those seen in a planar "top" view) of both the bracket base 101 and ligation cover 102 advantageously present a generally smooth, continuous outer surface generally defining a rectangle with rounded corners, and in which the exterior labial surface is curved in two axes. In other words, the exterior labial surface is curved around longitudinal slide axis S, as well as being curved around a perpendicular latitudinal axis L. The compound two axis curvature advantageously presents a low profile, smooth, and substantially continuous labial surface. Such a configuration is advantageously substantially free of discontinuities (other than recess 104), particularly sharp angled discontinuities, crevices, and/or intricate structures which tend to attract and hold in debris, for example food. In addition, the compound curve and smooth shape prevent or minimize injury to the tongue or other tissues, particularly soft tissues, found inside the mouth. Other shapes (e.g., substantially oval or round) that are also smooth and continuous (i.e., substantially without crevices, intricate structures, or other discontinuities) may also be possible. One such tear drop configuration is illustrated and described in conjunction with FIGS. 6A-6B. This smooth continuous surface, which is substantially free of crevices, discontinuities, or other small, intricate structures, prevents and/or reduces potential injury and discomfort to the patient, as well as minimizing the tendency for food or other foreign debris from catching, adhering, or otherwise becoming lodged within crevices of the orthodontic bracket 100.

As further illustrated in FIGS. 1A and 1B, ligation cover 102, while in a completely closed position relative to the bracket base 101, covers or occludes arch wire slot 106 designed to receive therein an arch wire. In an open position (FIG. 1A), cover 102 may be slid incisally so that slot 106 is completely unoccluded by cover 102, facilitating quick and easy insertion and/or removal of an arch wire while minimizing interference from cover 102. Ligation cover 102 may advantageously be provided with a bearing extension (not shown) designed to bear against and hold an arch wire in slot 106 (i.e., so as to provide active ligation) when ligation cover 102 is slid closed relative to the bracket base 101 and slot 106. The illustrated example further includes ligature grooves 107 on both the gingival and incisal edges of the bracket. Although traditional ligatures may be used in addition to the ligation cover 102, the ligation cover 102 generally provides sufficient ligation of arch wire 102 such that grooves 107 are optional. One advantage of including grooves 107 is that in the event a ligation cover breaks off, it is still possible for the practitioner to use the ligature grooves 107 and one or more ligatures (e.g., an elastomeric o-ring) to hold the arch wire in place, rather than replacing the broken bracket.

As shown in FIGS. 1A and 1B, base 101 may advantageously include a supporting ledge 108 adjacent to slot 106. Ledge 108 provides a surface against which a leading edge of cover 102 may be supported when closed (FIG. 1B). Such a configuration prevents cover 102 from being cantilevered over slot 106 when in a closed position, providing support to cover 102 so as to better resist any forces that may be applied in a lingual direction against the portion of cover 102 which is supported by ledge 108.

Figure 2A:
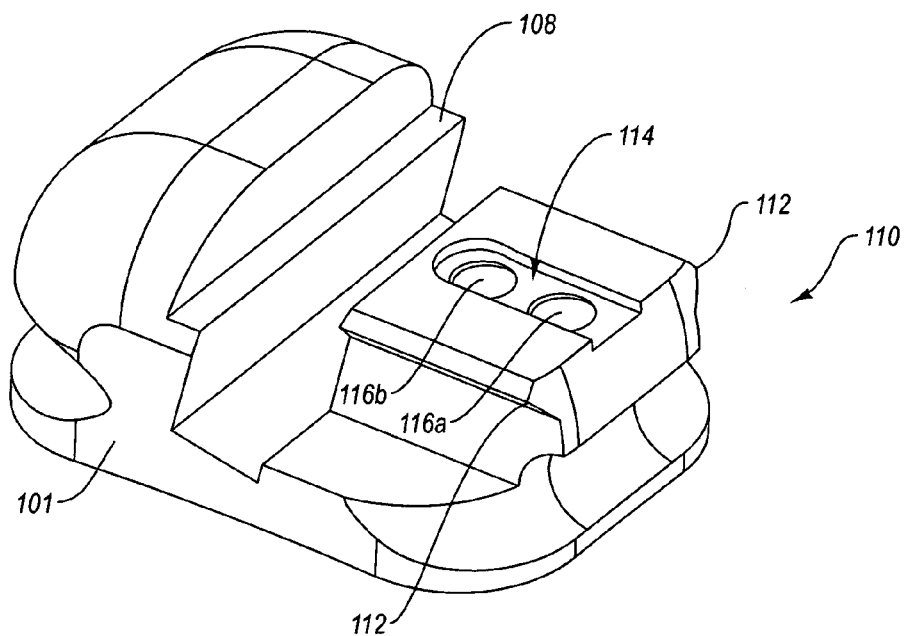
FIG. 2A is a perspective view of the bracket base portion of the bracket of FIG. 1A.
Figure 2B:
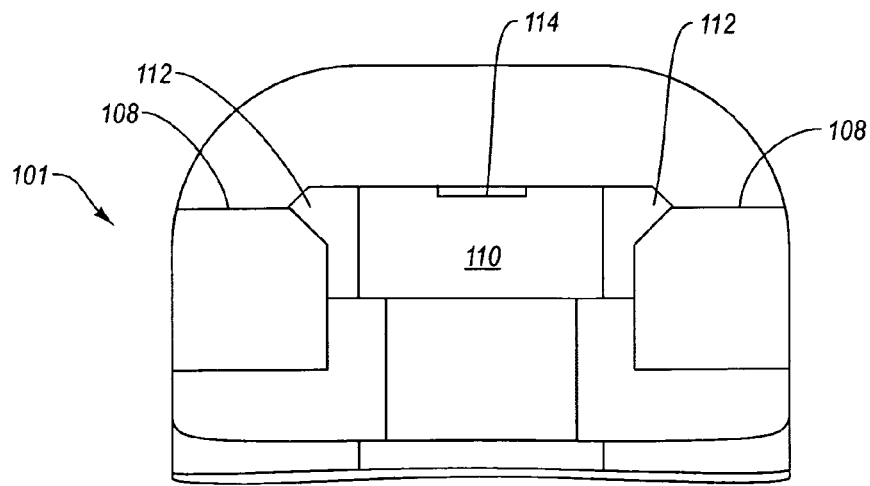
FIG. 2B is an end view of the bracket base of FIG. 2A.

FIGS. 2A-2B illustrate a perspective view and incisal end view, respectively, of bracket base 101 without an attached ligation cover 102. As shown, base 101 includes a sliding engagement mechanism for slidably coupling cover 102 to base 101. Illustrated base 101 includes a centrally disposed raised track 110 which extends labially from base 101. A pair of elongate rails 112 extend laterally from raised track 110. Rails 112 are oriented and aligned so as to be parallel with one another and to be parallel with axis S, defining a planar slide path. Elongate rails 112 and track 110 are configured to slidingly engage with corresponding structure formed on ligation cover 102, as later described and illustrated in conjunction with FIGS. 3A and 3B.

As perhaps best seen in FIG. 2A, labial surface of raised track 110 includes a groove 114 formed therein, with deepened wells 116a and 116b disposed at or near each end of groove 114. Groove 114 is configured to mate with and guide movement of a detent or other protrusion formed on the lingual surface of cover 102 as cover 102 slides over bracket base 101. Wells 116a and 116b are formed at locations corresponding to the desired location of the detent within cover 102 when the cover is fully open and fully closed, respectively. When latched open, the detent or other protrusion engages within well 116a. Well 116a and a detent or other protrusion formed on cover 102 are one example of latch means for holding the ligation cover in an open position when open. Well 116b and a detent or other protrusion on cover 102 are one example of latch means for holding ligation cover closed when closed. Other mechanisms for accomplishing similar function will be apparent to one skilled in the art.

Figure 3A:
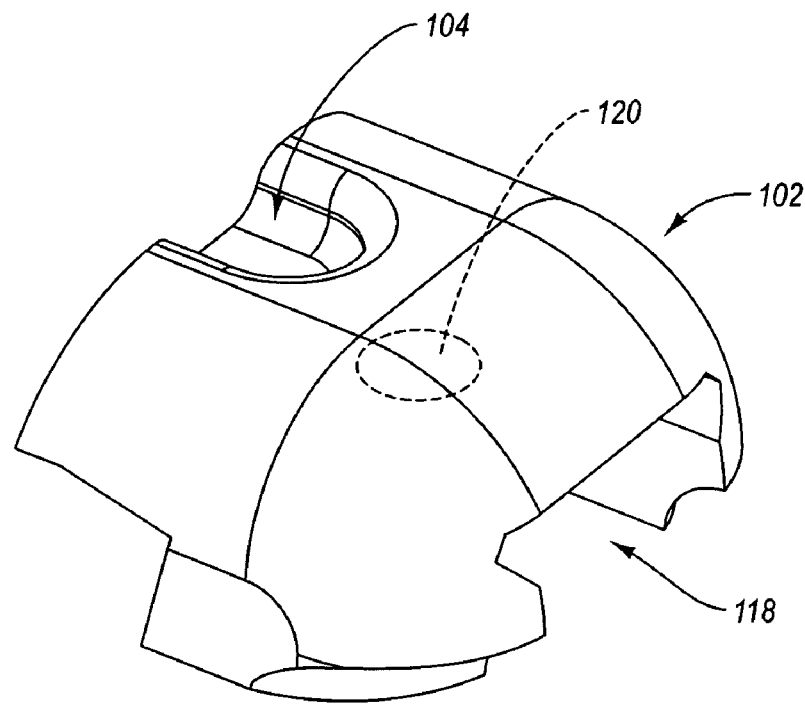
FIG. 3A is a perspective view of the sliding ligation cover portion of the bracket of FIG. 1A.
Figure 3B:
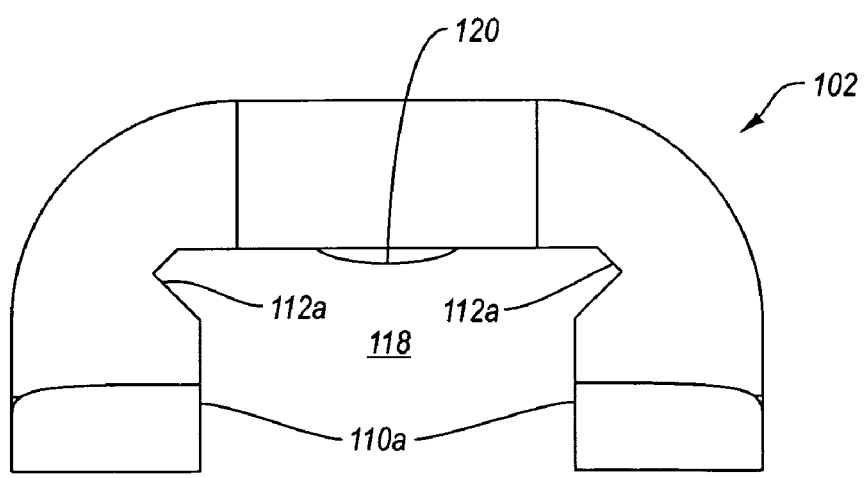
FIG. 3B is an end view of the ligation cover of FIG. 3A.

FIGS. 3A and 3B illustrate a perspective view and an incisal end view of the ligation cover 102, respectively. An interior, lingual surface of cover 102 includes a recess 118 having a shape corresponding to the track 110 and rails 112 of base 101 (FIGS. 2A-2B). This configuration allows ligation cover 102 to be aligned with base 101 along slide axis S and pressed so that track 110 and rails 112 engage the walls 110a and 112a defining recess 118, providing sliding engagement between cover 102 and base 101. A protrusion (e.g. detent 120) is also advantageously formed on a lingual surface of cover 102, extending into recess 118. Detent 120 slides within and is guided by groove 114, providing an additional guide surface (e.g., in addition to engagement between walls 110a and track 110 and between walls 112a and rails 112) that guides sliding movement of bracket cover 102 over base 101 along planar slide axis S. In addition, detent 120 may be sized so as to have a height slightly greater than the depth of groove 114 so that when it becomes aligned with either of wells 116a or 116b, it engages with the well to a depth greater than groove 114, latching the cover in an open position (in the case of well 116a) or a closed position (in the case of well 116b).

The ability of the bracket to hold the cover open when in an open position is advantageous, as it allows the orthodontic practitioner to more easily and quickly insert and/or remove the arch wire during a visit of the patient to the practitioner's office. In other words, it minimizes the possibility that the cover will inadvertently close (e.g., under force of gravity), requiring the practitioner to reopen the cover prior to inserting and/or removing an arch wire.

In addition, the sliding mechanism connection between the ligation cover and the bracket base is advantageous as it is more robust and more quickly opened and/or closed as compared to rotating hinge type connections. Furthermore, the operation of hinge type connections sometimes results in discomfort and/or pain for the patient, as a component of force applied to open the cover is transferred to the underlying tooth, which can be somewhat painful if a relatively large force is required in order to open or close the cover (e.g., as the result of a latch mechanism). In contrast, operation of the sliding mechanism of the present inventive bracket is more efficient in isolating applied forces from being transferred to the underlying tooth, resulting in increased comfort for the patient during adjustments at the office of the orthodontic practitioner It will be noted that the illustrated configuration of track 110, rails 112, and recess 118 provide a planar slide path along which the ligation cover 102 travels. Such a planar slide path is preferable to a curved slide path, which would require a significantly more complex movement technique by the practitioner. Also, the planar slide path configuration is significantly less expensive and complex to manufacture. Reducing complexity of manufacture is particularly important in the orthodontic bracket arts, as the brackets are extremely small.

Features such as providing an unoccluded slot 106 when cover 102 is open and providing latch mechanisms for holding the cover open when open are advantageous as they provide improved access when inserting or removing an arch wire from slot 106 as compared to a configuration where cover 102 is always biased to an occluding or closed position, or where the ligation cover 102 still substantially occludes or covers slot 106, even when fully open. In addition, configuring the sliding cover so that it slides open towards the incisal edge of the patient's tooth improves visual sight lines and physical access to the arch wire slot by the Examiner. As such, this configuration is preferred over one in which the cover slides gingivally to an open position.

The sliding engagement mechanism by which cover 102 is slidably attached to base 101 (i.e., track 110, rails 112, recess 118) is advantageously disposed within bracket 100, apart from the edges of the bracket, so as to allow cover 102 to cover substantially all of the internal structures of the mechanism when closed. This advantageously presents a relatively smooth and continuous outer surface with a minimum of crevices or intricate raised structures which may otherwise attract and trap food or debris. The described sliding mechanism is an example of means for slidably connecting ligation cover 102 to bracket base 101. Other sliding mechanisms and latch mechanisms which are internal (e.g., switching the positions of the track/rails and recess so that the track/rails are in the cover and the recess is in the base and/or switching the positions of the groove/wells and the detent so that the groove and a well are in the cover and one or more detents are in the base) will be apparent to one skilled in the art.

A bracket configuration consisting of only two parts (i.e., the bracket base and a ligation cover) is advantageous as it allows for very simple manufacture, assembly and dis-assembly of the orthodontic bracket, which is particularly helpful as the orthodontic brackets are very small (e.g., length of about 4 mm, width of about 2 mm, height of about 3 mm). As such, it can be quite difficult to orient the ligation cover 102 relative to the bracket base 101 as needed when assembling the bracket by hand. The illustrated embodiment only requires that the cover be aligned with the base, and then slid in. In other words, no twisting, bending of parts, etc. is required during the aligning and attachment process.

Figure 4:
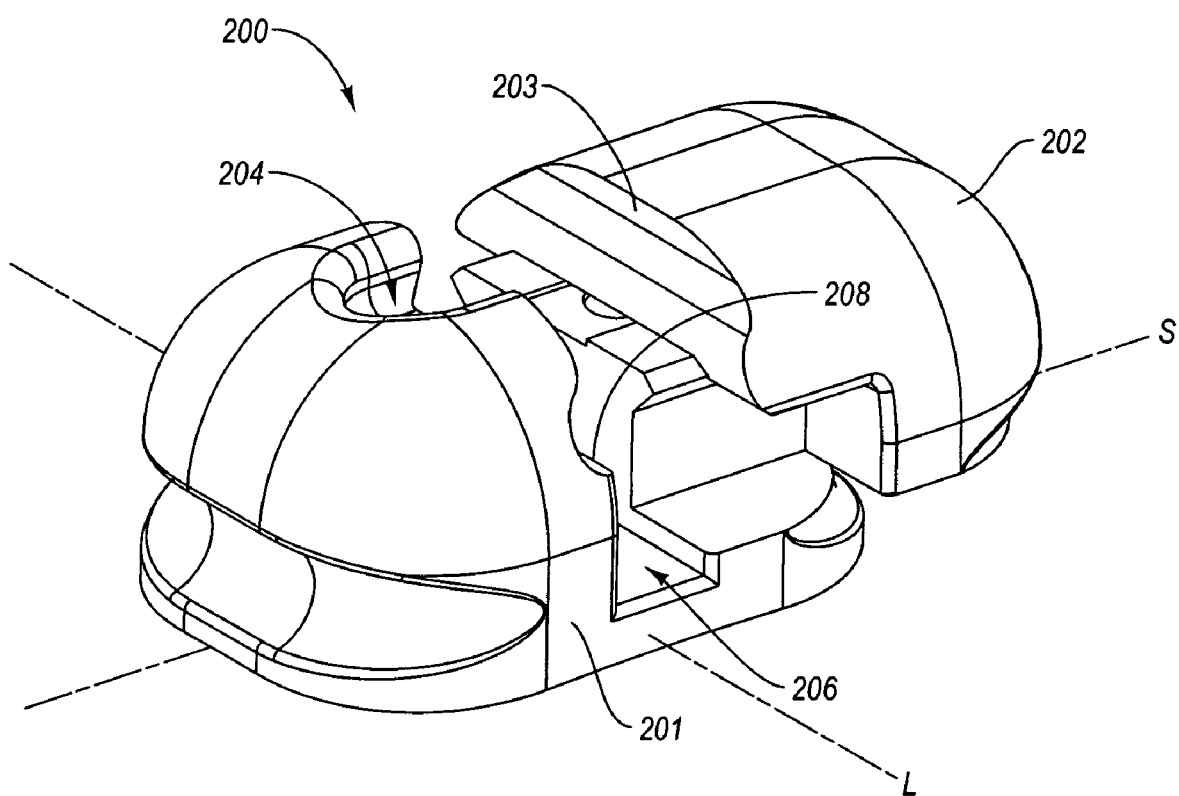
FIG. 4 is a perspective view of an alternative orthodontic bracket including a sliding ligation cover shown in an open position.

FIG. 4 illustrates an alternative bracket 200 including a bracket base 201 and a sliding ligation cover 202. A principal difference between bracket 200 and bracket 100 of FIGS. 1A and 1B is the location of recess 204. In bracket 200, recess 204 is actually formed within bracket base 201 rather than cover 202. Recess 204 is formed at the incisal edge of the labially exposed portion of base 201. Because of its different location, it functions somewhat differently than recess 104 used to open cover 102 of bracket 100. A dental scaler or other tool may be inserted within recess 204 so as to be positioned against leading gingival edge 203 of cover 202 and an incisally directed force applied to open cover 202 relative to slot 206. Such a configuration may further reduce any transmission of opening and/or closing forces to the underlying tooth so as to further minimize discomfort and/or pain experienced by the patient.

FIG. 4 also includes differences in the interface between cover 202 and base 201 adjacent the arch wire slot. The illustrated embodiment similarly includes a ledge 208 in base 201 within which leading gingival edge 203 of cover 202 is supported so as to prevent cover 202 from being cantilevered over the arch wire slot when closed, although the contact interface between cover 202 and base 201 adjacent ledge 208 is convexly curved relative to cover 202 and complementarily concavely curved relative to base 201, rather than the straight and angular configuration of FIGS. 1A-1B. Engagement between leading gingival edge 203 and ledge 208 prevents both up and down cantilevered movement of cover 202 when in the closed position.

Figure 5A:
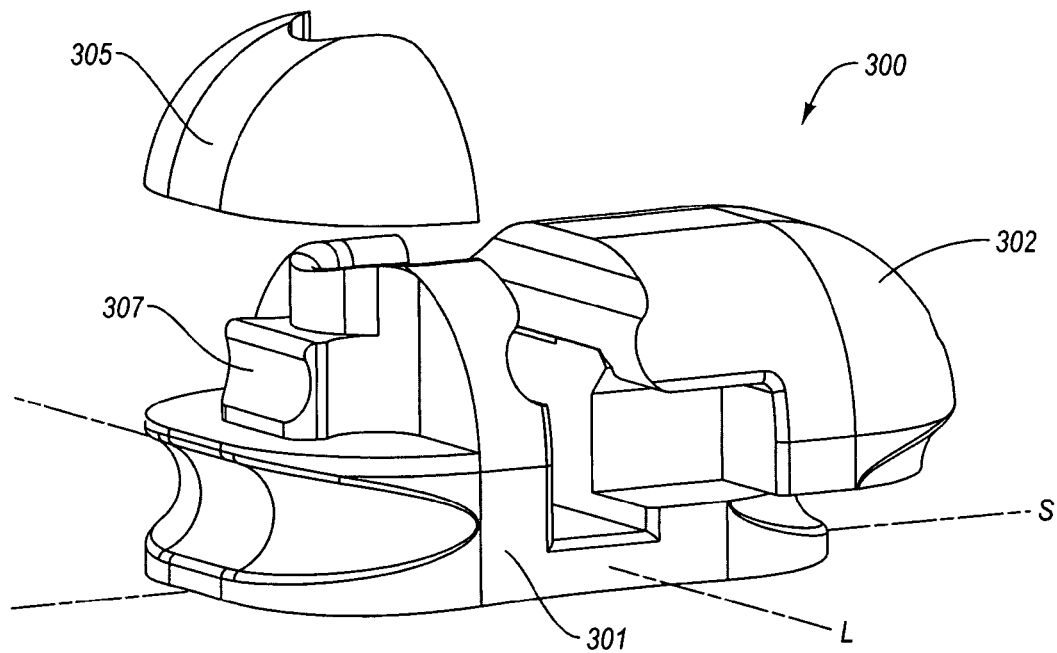
FIG. 5A is an exploded perspective view of an alternative 3-piece orthodontic bracket similar to that of FIG. 4, but with an aesthetic insert portion for the bracket base.
Figure 5B:
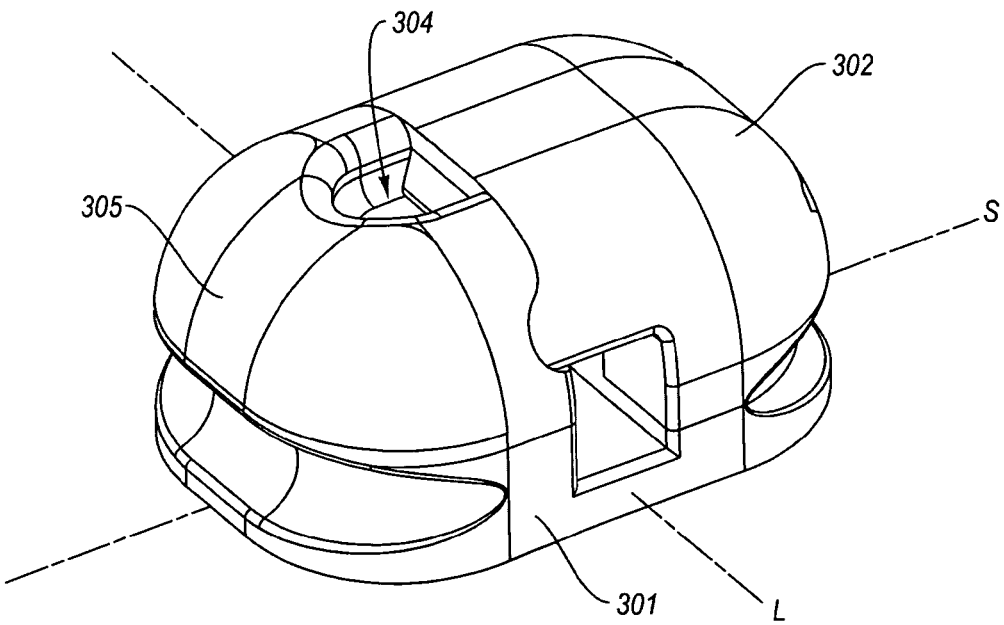
FIG. 5B is a perspective view of the bracket of FIG. 5A in an assembled and closed configuration.

FIGS. 5A and 5B illustrate another alternative bracket 300 including a bracket base 301 and sliding ligation cover 302. Bracket 300 is similar to bracket 200 of FIG. 4. In addition, bracket 300 is illustrated as comprising a 3-piece bracket, whereas brackets 100 and 200 are illustrated as 2-piece brackets (consisting of a bracket base and a ligation cover, with no additional parts). Bracket base 301 of bracket 300 includes an interchangeable aesthetic insert 305, which may be removed and replaced with another insert, as desired. Such an embodiment allows the practitioner and patient some flexibility in creating a desired aesthetic appearance. For example, because cover 302 can be separated from base 301 by sliding it incisally, the practitioner may replace a cover 302 which has become soiled, stained, lost, broken, or simply upon request of the patient (e.g., the patient may desire to replace a metal ligation cover with a brightly colored polymeric resin or ceramic ligation cover).

Figure 10:
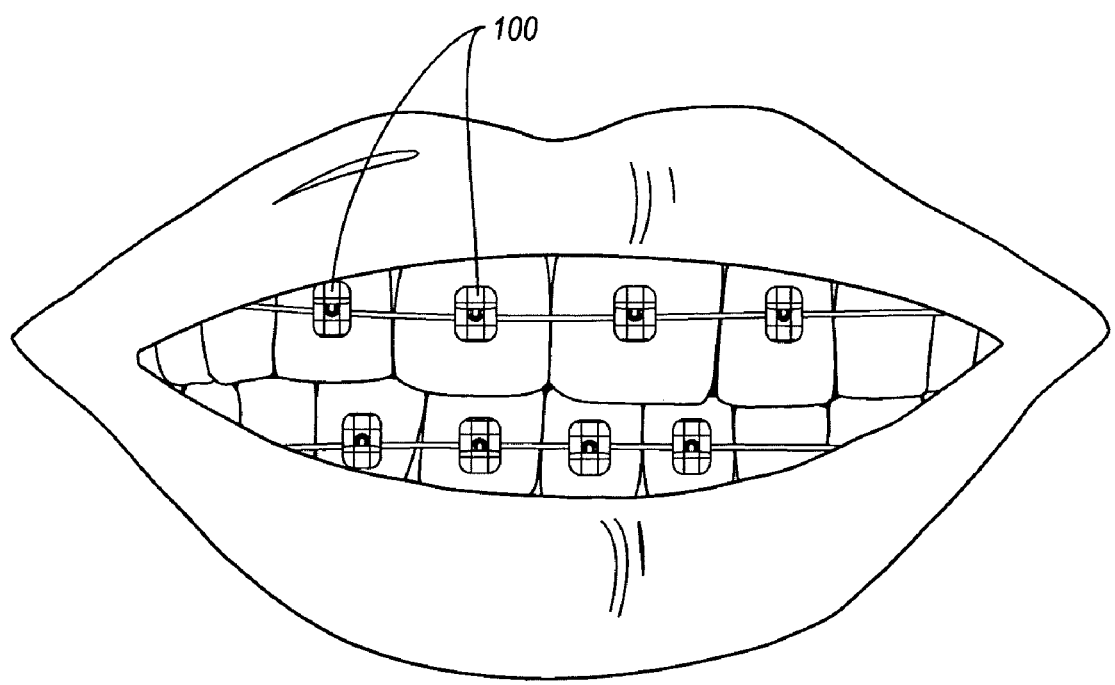
FIG. 10 is a perspective view of a plurality of the orthodontic brackets of FIG. 1A, each bracket being attached to the tooth of a patient.

A matching (or contrasting, as desired) insert 305 may also be installed at the same time. Insert 305 slides lingually, from a position as illustrated in FIG. 5A to an installed position as shown in FIG. 5B, in which a recess (not shown) within the insert 305 engages with mating protrusion 307. It will also be apparent that this configuration allows the practitioner to replace substantially all of the visible labial exterior surface of the bracket as viewed when installed, which is advantageous as it allows a patient to create a desired "look". For example, cover 302 and insert 305, which comprise substantially all of the viewable surface of the brackets when installed (except the small region of base 301 which is exteriorly exposed) may appear pink, yellow, blue, green, red, orange, purple, or any other bright and/or contrasting color relative to the tooth color. As perhaps best seen in FIG. 10, it is the compound curved labial exterior surfaces of brackets 100 which are visible when worn, such that the mesial and distal "sides" of the bracket are nearly or completely obscured.

Figure 6A:
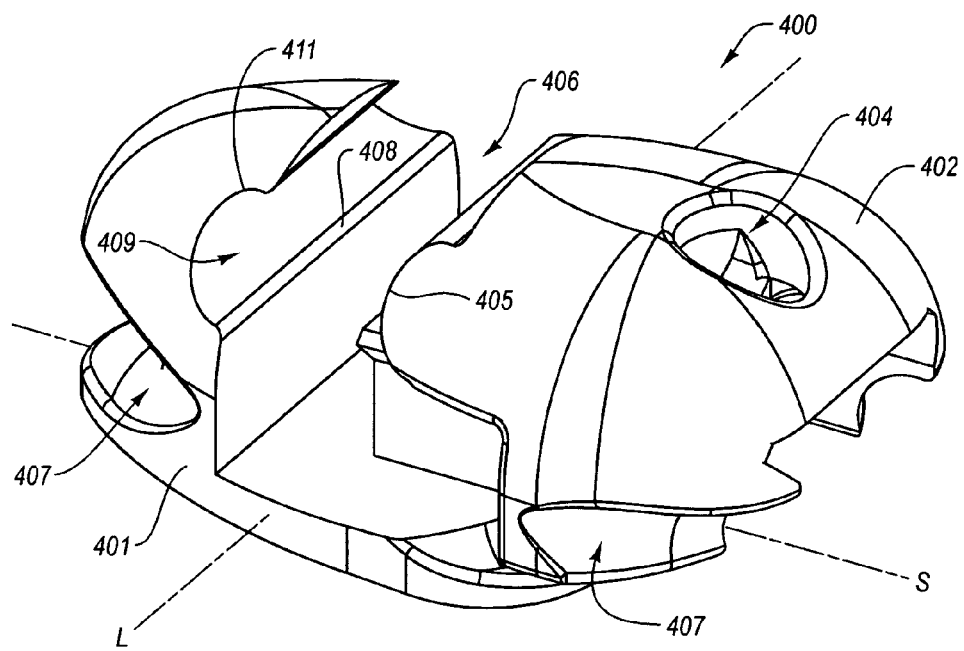
FIG. 6A is a perspective view of an alternative bracket including a sliding ligation cover shown in an open position, the bracket having a tear drop shape.
Figure 6B:
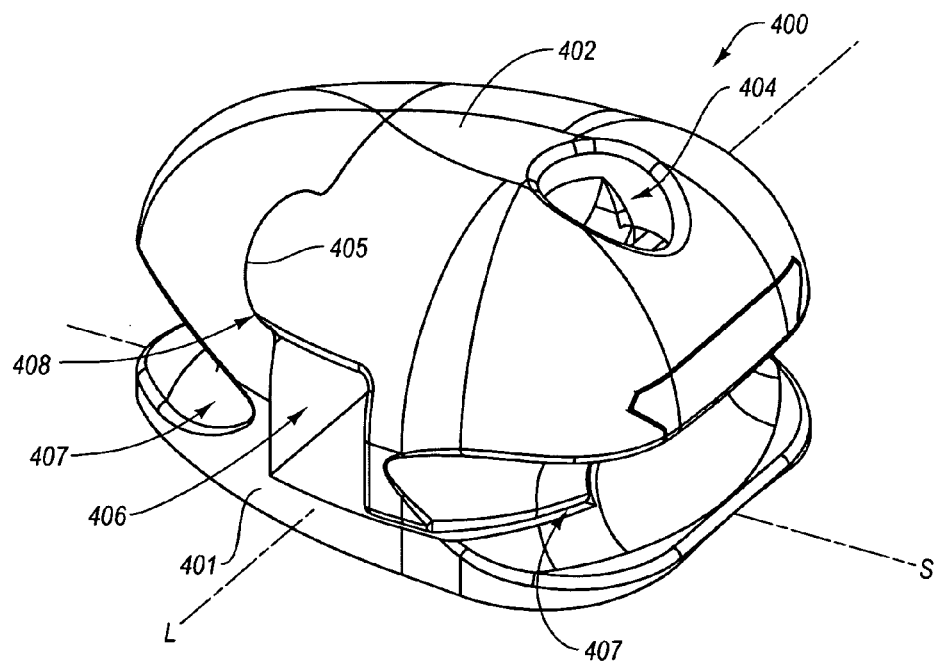
FIG. 6B is a perspective view of the bracket of FIG. 6A in a closed configuration.

FIGS. 6A and 6B illustrate another alternative bracket 400, which includes a bracket base 401 and sliding ligation cover 402. Bracket 400 is configured so that the exterior labial surface of the bracket base and ligation cover form a teardrop shape. Such a bracket may be particularly suited for installation on the lower incisors. An arch wire slot 406 and ligature grooves 407 are provided, similar to bracket 100 of FIGS. 1A-1B. Bracket 400 includes a through hole 404, which is positioned just incisally of the center of cover 402. A practitioner is able to insert a dental tool into hole 404 and pull the cover 402 open, similar to the function of recess 104. Although configured as an open through hole (i.e., hole 404 runs completely through cover 402), a recess that is closed at a lingual bottom surface could alternatively be provided.

In addition, the gingival leading edge 405 of cover 402 and an opposite receiving ledge portion 408 of base 401 are complementarily configured so that convexly curved leading edge 405 of cover 402 is received within concavely curved receiving portion 409 of base 401. When closed, the gingival leading edge of cover 402 is supported from below (i.e., lingually) by ledge 408. In addition, a labial uppermost portion 411 of base 401 wraps over the top of the leading edge of cover 402, helping to guide it into place during closure. In other words, leading edge 408 becomes sandwiched between lower lingual ledge 408 and the labial uppermost portion 411 of base 401, thus preventing both upward and downward cantilevered motion of the cover 402.

Figure 6C:
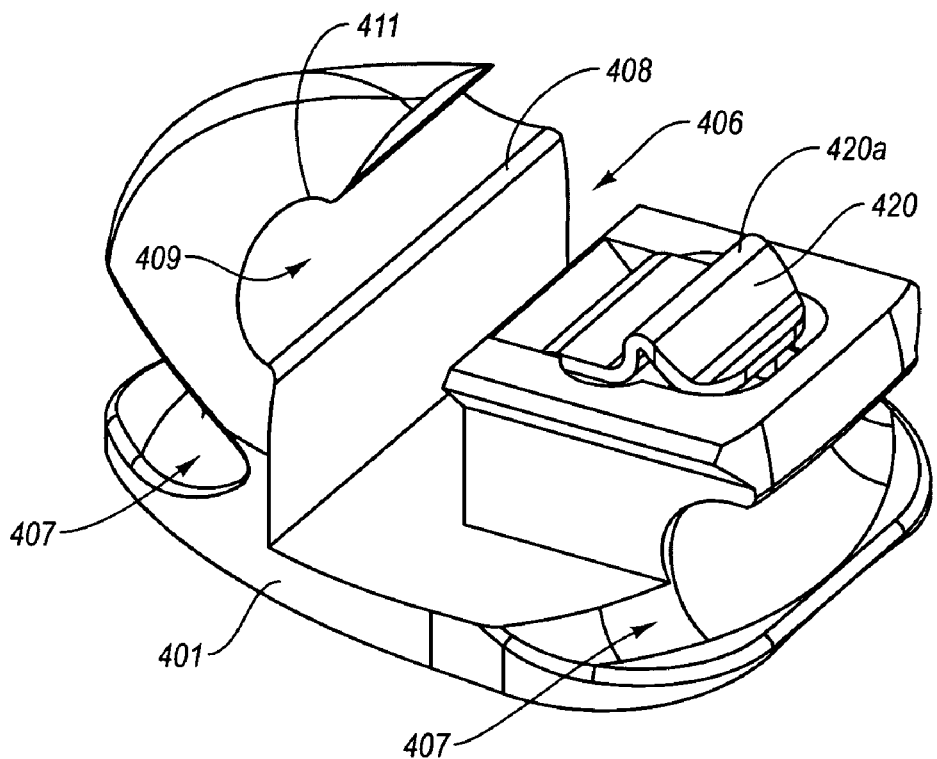
FIG. 6C is a perspective view of the bracket base portion of the bracket of FIG. 6A.
Figure 6D:
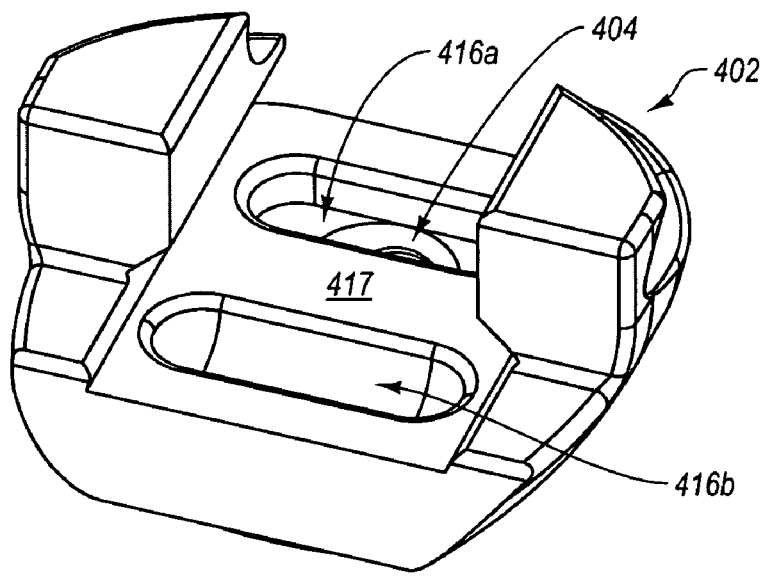
FIG. 6D is a inverted perspective view of the sliding ligation cover portion of the bracket of FIG. 6A.
Figure 6E:
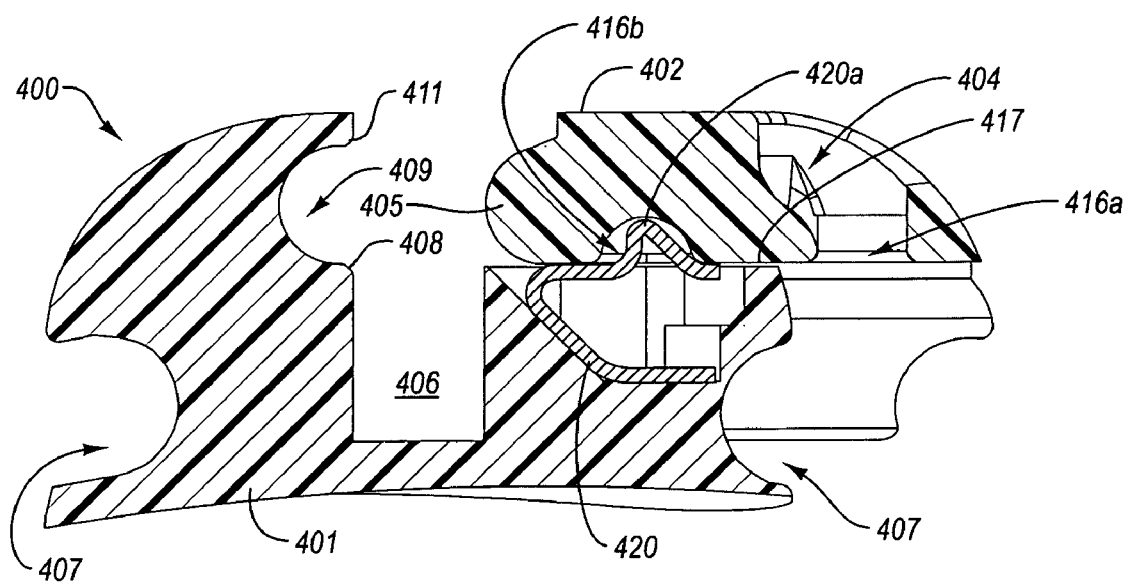
FIG. 6E is a cross-sectional view of the bracket of FIG. 6A in an open position.
Figure 6F:
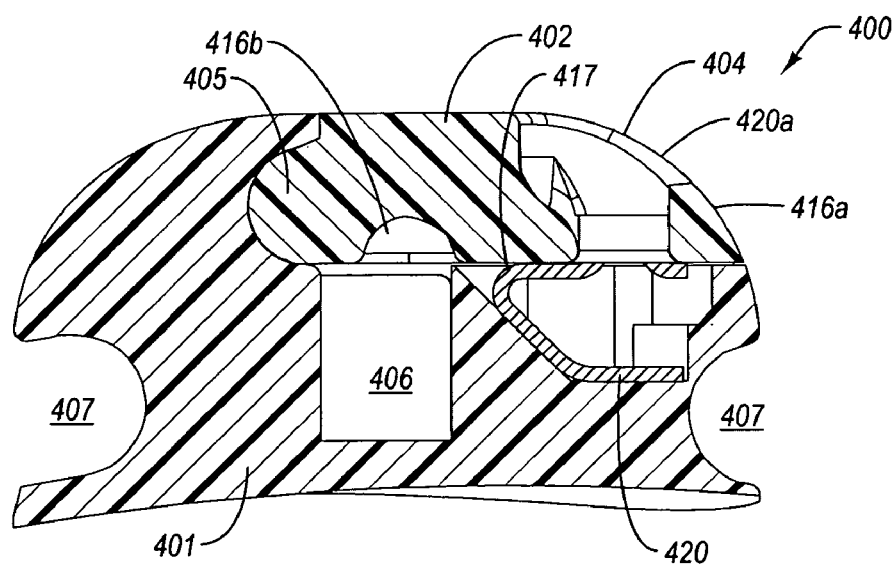
FIG. 6F is a cross-sectional view of the bracket of FIG. 6A in a closed position.

FIGS. 6C-6F illustrate an alternative latch means illustrated in conjunction with bracket 400. Bracket 400 is shown as a 3 piece bracket. FIG. 6C shows base 401, with a separate resilient spring member 420. Spring member 420 is illustrated as a U-shaped clip, with one leg of the U being hidden within bracket base 401. This unseen leg of the clip serves to attach the clip to base 401. Separated cover 402 is illustrated inverted in FIG. 6D, so as to better show the latch mechanism of cover 402 which engages with spring member 420. The hidden internal surface of cover 402 includes a first well 416a and a second well 416b, each of which are illustrated as oblong (or elongated) so as to receive elongated raised portion 420a of spring member 420. Raised portion 420a of spring member 420 is engaged within well 416a when cover 402 is closed, and engages within well 416b when cover 402 is open. Resilient spring member 420 is sufficiently resilient to allow raised portion 420a to deform by flattening downward when passing over portion 417 of cover 402 between wells 416a and 416b, and springs back labially upward when cover 402 is slid either fully open or closed so that raised portion 420a is aligned with either well 416b or well 416a, respectively. FIGS. 6E and 6F illustrate cross-sectional views of bracket 400 in the open and closed positions respectively, so as to clearly illustrate this. As best seen in these views, hole 404 may connect to well 416a.

Figure 7A:
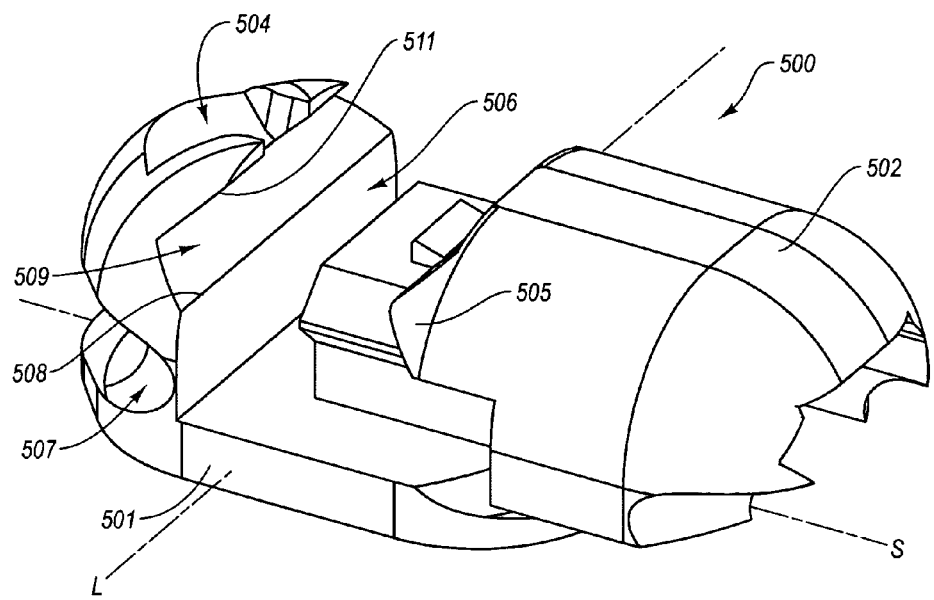
FIG. 7A is a perspective view of an alternative bracket including a sliding ligation cover shown in an open position, the bracket having a substantially oval shape.
Figure 7B:
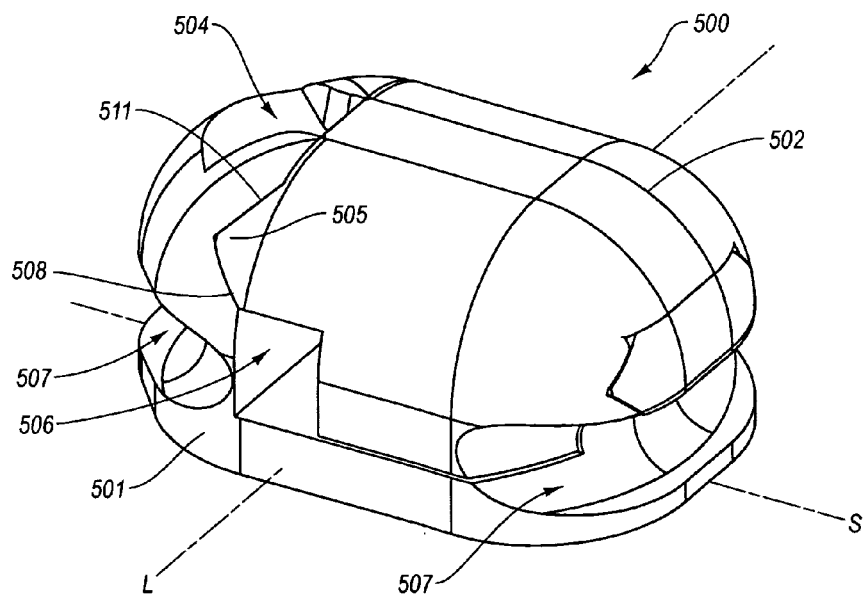
FIG. 7B is a perspective view of the bracket of FIG. 7A in a closed configuration.

FIGS. 7A and 7B illustrate another alternative bracket 500 including a bracket base 501 and sliding ligation cover 502. An arch wire slot 506 and ligature grooves 507 are provided, similar to bracket 100 of FIGS. 1A-1B. Bracket 500 includes a V or U shaped recess 504, which is more angular in shape than the U recess 104, and as such is less preferred. Recess 504 is formed in bracket base 501, similar to bracket 200 of FIG. 4. Gingival leading edge 505 of cover 502 and an opposite receiving ledge portion 508 of base 501 are complementarily configured so that gingivally projecting leading edge 505 is received within female receiving portion 509 of base 501. Similar to bracket 400, when closed, the gingival leading edge 505 of cover 502 is supported from below (i.e., lingually) by ledge 508. In addition, a labial uppermost portion 511 of base 501 extends over the top of the leading edge of cover 502, helping to guide it into place during closure and supporting gingival leading edge 505 from above. In other words, leading edge 508 becomes sandwiched between lower lingual ledge 508 and the labial uppermost portion 511 of base 501, preventing both upward and downward cantilevered movement of lower 502 when in the closed position.

Figure 7C:
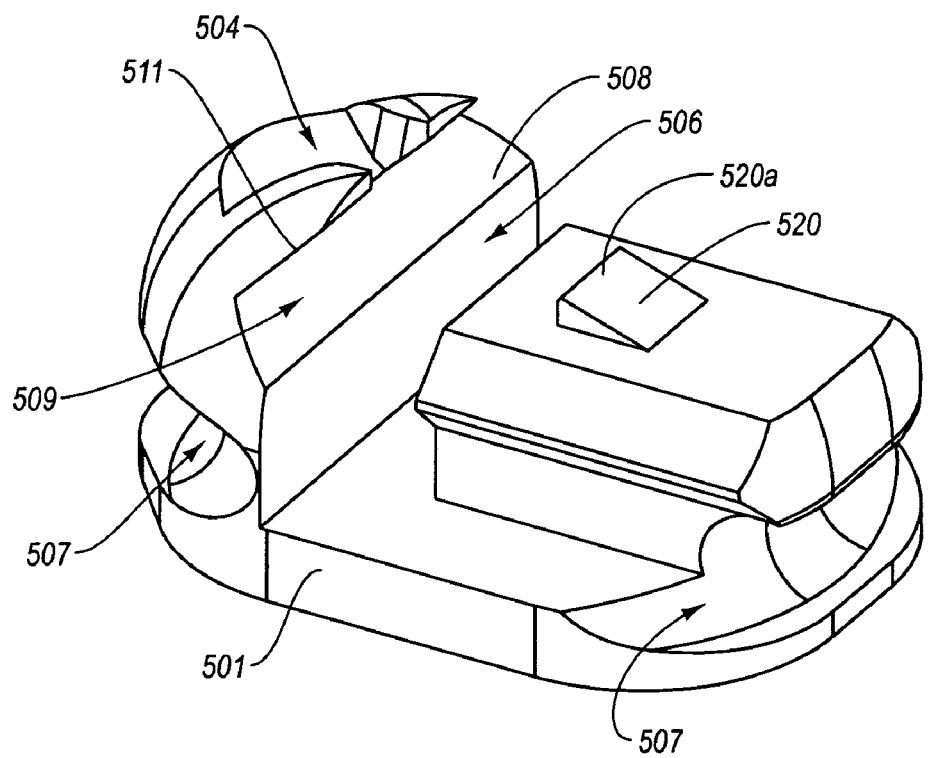
FIG. 7C is a perspective view of the bracket base portion of the bracket of FIG. 7A.
Figure 7D:
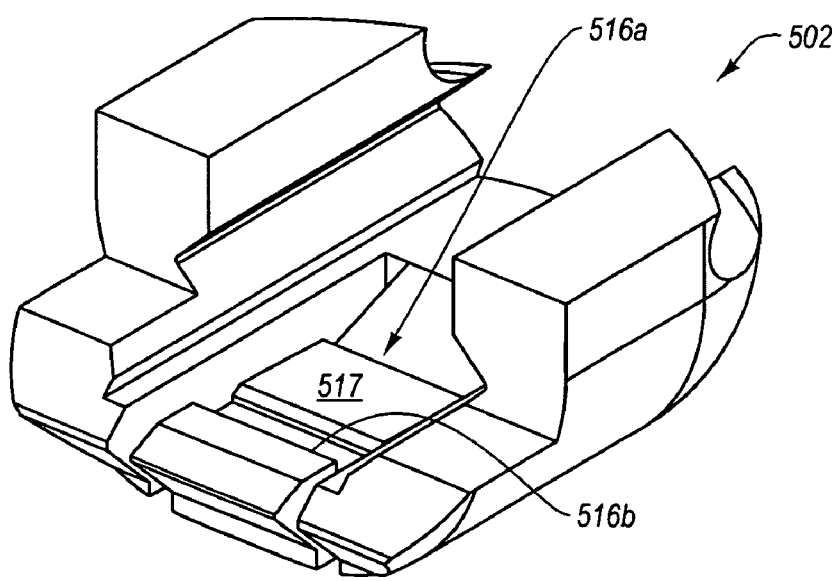
FIG. 7D is a inverted perspective view of the sliding ligation cover portion of the bracket of FIG. 7A.
Figure 7E:
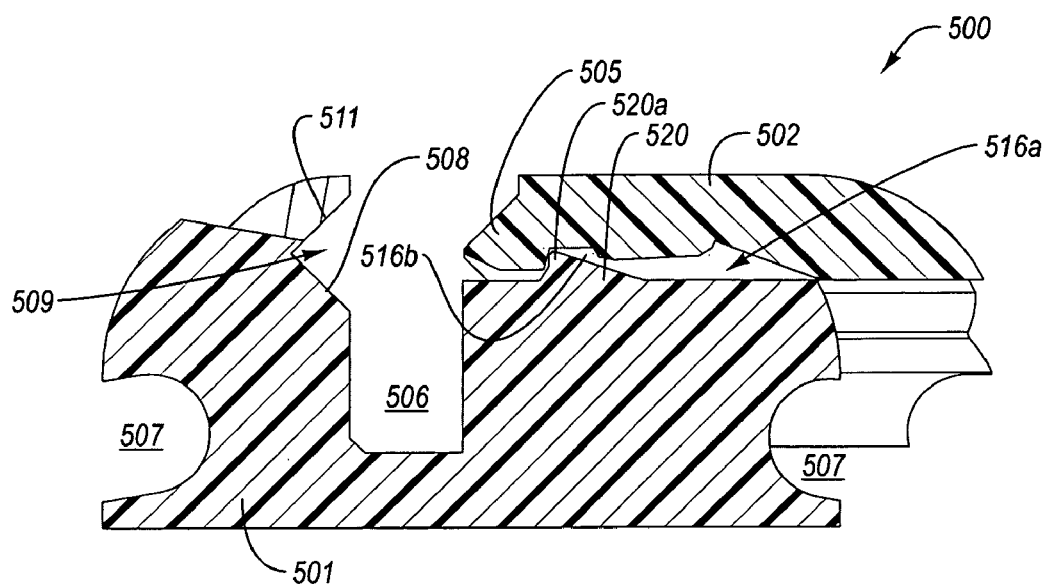
FIG. 7E is a cross-sectional view of the bracket of FIG. 7A in an open position.
Figure 7F:
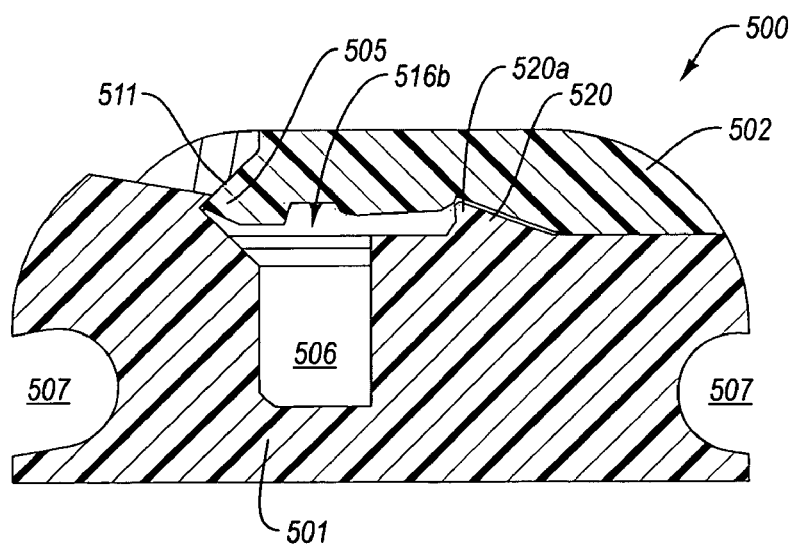
FIG. 7F is a cross-sectional view of the bracket of FIG. 7A in a closed position.

FIGS. 7C-7F illustrate another alternative latch means illustrated in conjunction with bracket 500. Bracket 500 is a 2 piece bracket. FIG. 7C shows base 501, with an integral ramp shaped protrusion 520. Separate cover 502 is illustrated in an inverted position in FIG. 7D, so as to better show the latch mechanism of cover 502 which engages with ramp protrusion 520. The hidden internal surface of cover 502 includes a complementarily ramped first well 516a and a second well 516b, each having a width so as to receive raised portion 520a of ramp 520. Raised portion 520a of spring member 520 is engaged within ramped well 516a when cover 502 is closed, and engages within well 516b when cover 502 is open. Ramp 520 and/or surrounding wells 516a and 516b of cover 502 are sufficiently resilient to allow raised portion 520a to pass over portion 517 of cover 502 between ramped well 516a and well 516b, and springs back labially upward when cover 502 is slid either fully open or closed so that raised portion 520a is aligned with either well 516b or ramped well 516a, respectively. FIGS. 7E and 7F illustrate cross-sectional views of bracket 500 in the open and closed positions respectively, so as to clearly illustrate this.

Figure 8A:
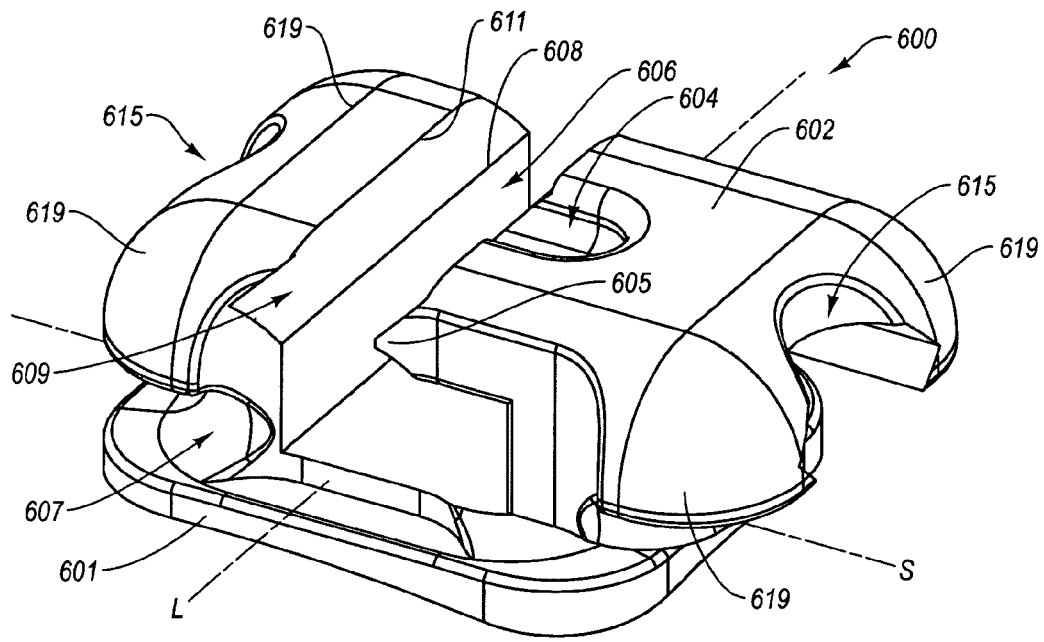
FIG. 8A is a perspective view of an alternative bracket including a sliding ligation cover shown in an open position, the bracket having a substantially rectangular shape modified to include four tie wings.
Figure 8B:
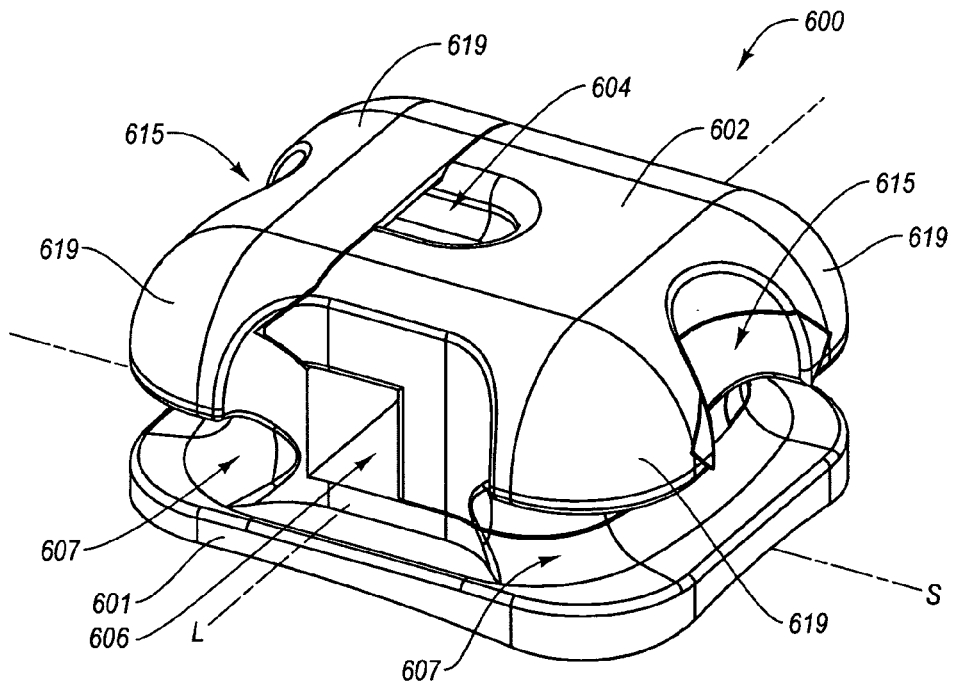
FIG. 8B is a perspective view of the bracket of FIG. 8A in a closed configuration.

FIGS. 8A and 8B illustrate another alternative bracket 600, which includes a bracket base 601 and sliding ligation cover 602. An arch wire slot 606 and ligature grooves 607 are provided, similar to bracket 100 of FIGS. 1A-1B. Bracket 600 includes a U shaped recess 605 similar to U shaped recess 104 of bracket 100. Gingival leading edge 605 of cover 602 and an opposite receiving ledge portion 608 of base 601 are complementarily configured so that gingivally projecting leading edge 605 is received within female receiving portion 609 of base 601. Similar to bracket 500, when closed, the gingival leading edge of cover 602 is sandwiched between ledge 608 and labial uppermost portion 611 of base 501.

Bracket 600 is configured so that the exterior labial surface of the bracket base and ligation cover present a substantially rectangular shape, which is modified by incisal and gingival cut away portions 615 so as to provide a "twin" type bracket having four tie wings 619 when the cover 602 is in the closed position. One advantage of bracket 600 is that the gingival tie wings 619 are formed as a portion of base 601, and incisal tie wings 619 include a portion provided by cover 602 and a portion provided by base 601. As such, in the event that cover 602 becomes broken, the base portions of the tie wings 619 still remain, and so the bracket can be ligated with traditional o-ring ligatures without requiring removal and replacement of the bracket base.

Figure 9A:
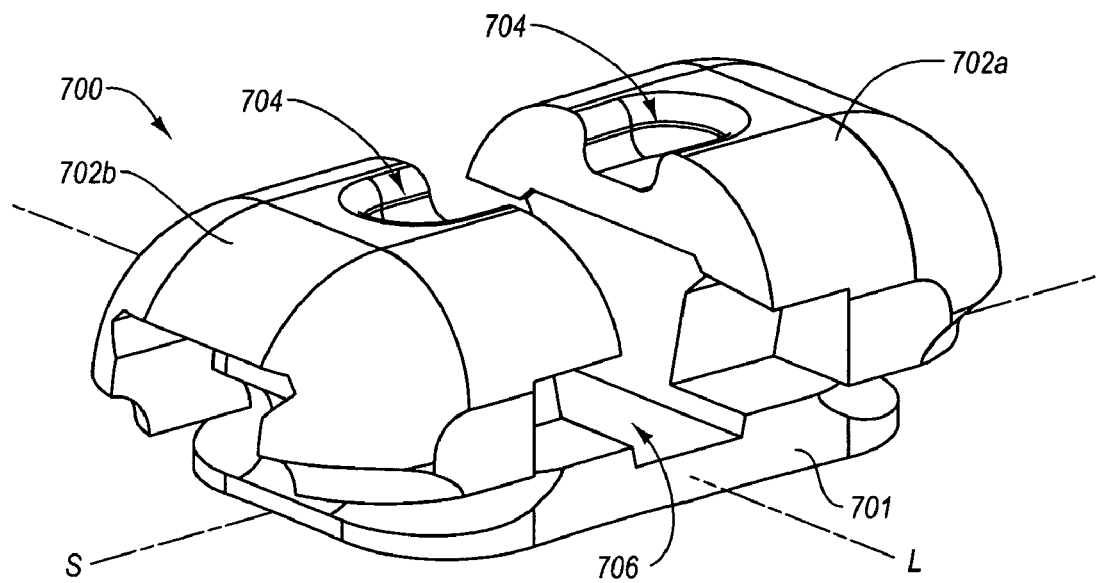
FIG. 9A is a perspective view of an alternative orthodontic bracket including two co-linear ligation covers shown in an open position.
Figure 9B:
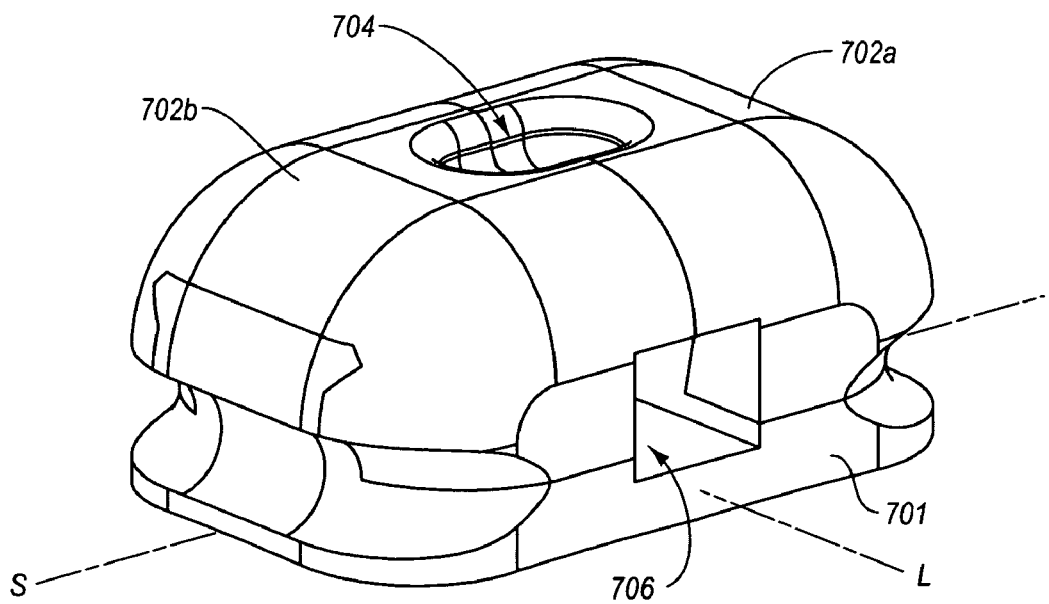
FIG. 9B is a perspective view of the orthodontic bracket of FIG. 9A with the ligation covers in a closed position relative to the bracket base.

FIGS. 9A and 9B illustrate another alternative bracket 700 in which both the gingival and incisal sides of the bracket close over arch wire slot 706; in effect, bracket 700 includes two ligation covers 702a and 702b. Each cover includes a U shaped portion of an oval or circular recess 704. The sliding and latching mechanism by which each cover 702a, 702b engages with bracket base 701 may be similar to that illustrated in conjunction with FIGS. 1A-3B of bracket 100, or any of the other illustrated brackets. Another principal difference (besides the presence of two ligation covers 702a and 702b) is that when in a closed position (FIG. 9B), the leading edge of each cover is cantilevered over slot 706, rather than being supported by a ledge. Although unsupported by a ledge, bracket 700 exhibits other advantages relative to the other illustrated embodiments. For example, the presence of the two oppositely disposed co-linear covers 702a and 702b allow the practitioner to "pinch" the bracket between two fingers to close the bracket. Each cover is only required to move half as far as embodiments that include a single cover. Because both sides of the bracket move in such a pinching motion, very little if any force is transferred to the underlying tooth. As such, an embodiment including two ligation covers which move towards one another so as to occlude the arch wire slot may provide for superior patient comfort.

In each illustrated embodiment, the exposed labial surface of the cover and any exposed labial surface of the bracket base include a compound, two axis curvature so as to be symmetrically curved relative to both the longitudinal as well as latitudinal axis. These labial exterior surfaces are smooth and substantially free of crevices, discontinuities and/or any other intricate structures. Minimization or elimination of such structures prevents or minimizes accumulation of food or other debris within such tiny crevices. Any included recess or opening (e.g., the opening recess) is preferably a single recess which is preferably U shaped or other smoothly curved shape (e.g., O shaped—similar to through hole 404 of bracket 400) so as to provide a smooth surface, minimizing any tendency of such recess to interfere with the ability of the bracket to resist accumulation of debris. As such, the labially exposed portions of the bracket advantageously present a substantially smooth and substantially continuous outer surface, which is more comfortable for the patient and provides less opportunity for accumulation of food and debris.

According to one such embodiment, the labially exposed portion of the bracket presents a substantially rectangular, ovular, or teardrop configuration with compoundly rounded edges (i.e., simultaneously curved around two axes). The compound rounded edges may be generously rounded, e.g., having a radius of curvature at least about 0.010 inch, more preferably 0.020 inch, most preferably at least about 0.030 inch. For example, the illustrated examples include radii of curvature between about 0.030 and about 0.040 inch. Such generously curved surfaces are much more smooth than those typical of orthodontic brackets (e.g., no more than about 0.005 inch). Such compound curvatures provide a low profile bracket, and in combination with the smooth, continuous nature of the exterior labial surface of the bracket, results in reduced accumulation of debris and food around the bracket during use.

The bracket base and ligation cover of the orthodontic bracket may be formed of various materials. According to one embodiment, the bracket base is formed of at least one of metal, ceramic, glass, or a polymeric resin. The bracket base preferably is formed of a metal or ceramic material so as to impart a high degree of strength to the bracket base, particularly the area surrounding the arch wire slot. The ligation cover is formed of at least one of metal, ceramic, glass, or a polymeric resin. Exemplary ceramic materials include, but are not limited to, aluminous oxide, zirconia, and porcelain. Examples of suitable metals include, but are not limited to, stainless steel, stainless steel alloys, titanium, nickel-titanium alloys, and liquid metal, an amorphous zirconium based metallic alloy.

Preferred polymeric resin materials from which the bracket base and/or ligation cover may be formed include numerous thermoplastic materials. Examples of suitable thermoplastic materials include, but are not limited to, polyamides (crystalline or amorphous), acetal polymers, polyetherimides, polycarbonates, polyarylether ketones, Z polysulfones, and polyphenylsulfones.

Specific exemplary polymeric resin materials useful in forming orthodontic bracket bases and/or ligation covers include TROGAMID, a crystalline polyamide manufactured by Degussa AG, located in Germany; GRILAMID, an amorphous polyamide manufactured by EMS-CHEMIE AG, located in Germany; PEEK, a polyarylether ketone manufactured by Victrex USA, Inc., located in Greenville, S.C.; and RADEL, a polyphenylsulfone manufactured by Solvoy S.A., located in Brussels, Belgium.

Additional suitable polymeric resin materials and specific characteristics of the above polymeric resin materials and orthodontic bracket components formed therefrom, including methods for coating the bracket components for increased hardness and deformation resistance, are disclosed in U.S. application Ser. No. 10/835,959, filed Apr. 30, 2004, and entitled ORTHODONTIC BRACKETS MADE FROM POLYMERIC MATERIALS THAT IMPART DESIRED STRENGTH PROPERTIES, and U.S. application Ser. No. 11/045,948, filed Jan. 28, 2005, and entitled ORTHODONTIC BRACKETS COATED TO INCREASE RESISTANCE TO WEAR AND DEFORMATION, both of which are hereby incorporated by reference. Although it may be possible to form the bracket base and/or ligation cover from a polymeric resin material, metals and ceramics are preferred for their superior deformation resistance.

According to one embodiment, the ligation cover and/or bracket base may be colored through incorporation of a dye or pigment into the forming material, especially where the bracket component is formed from glass or a polymeric resin material. The colored dye or pigment may comprise any desired color (e.g., red, white, blue, green, orange, black, yellow, purple, tooth colored, colorless, etc.). Bright and/or high contrast colors may be preferred by patients desiring to draw attention to their brackets, while low contrast colors (e.g., white, colorless, or tooth colored) may be preferred by patients wanting to hide or draw minimal attention to their brackets.

Alternatively, the ligation covers and/or bracket bases may include a colored coating. Colored coatings may be particularly preferred as a means of coloring the bracket component where the covers are formed from metal or ceramic. Such a coating (e.g., a ceramic) may give a metal ligation cover and/or bracket base any desired color. Decorative images, graphics, figures, patterns, designs and/or other decorations may also be added, as desired. Additional details and methods of either incorporating a dye or pigment into the forming material or applying a coating which may be colored are disclosed in U.S. Pat. No. 7,134,872, U.S. patent application Ser. No. 11/613,767, filed Dec. 20, 2006 and entitled COLORED ORTHODONTIC BRACKETS HAVING REMOVABLE LIGATION COVER, and U.S. patent application Ser. No. 11/045,948, filed Jan. 28, 2005, and entitled ORTHODONTIC BRACKETS COATED TO INCREASE RESISTANCE TO WEAR AND DEFORMATION, each of which is hereby incorporated by reference with respect to its disclose of incorporating a colorant into a bracket forming material and/or applying a coating which may be colored.

In addition to decorative images, graphics, figures, patterns, or designs; other decorations, for example, decals, stickers, jewelry, or even small LED lights may be incorporated into or applied over the exposed labial portion of the brackets (i.e., the ligation cover and/or an insert portion of the bracket base). Such features, as well as high contrast colors (i.e., colors providing a high degree of contrast against the teeth, for example, fluorescent and/or bright colors) may be particularly desirable to those patients wishing to draw attention to their brackets. Other patients may instead want to minimize the appearance of their orthodontic brackets, and may choose for example, white, colorless (i.e., clear) or tooth colored ligation covers and/or bracket bases. Such options associated with the bracket advantageously allow each patient to tailor the aesthetic appearance of their overall bracket system to their particular tastes. In addition, because in at least some embodiments the ligation cover is removable from the bracket base as described above, the covers may be removed from the bracket bases (even while the bracket base is attached to the tooth) and replaced with a different cover having a different color, image, graphic, figure, pattern, designs, or other decoration during treatment.

Furthermore, it will be noted that when installed, the ligation cover largely hides the underlying bracket base from the view of someone looking at the patient. Such a characteristic is advantageous as it allows the user to create and change the appearance of the ligation covers while minimizing any color clashing or mismatching which might otherwise be undesirable between the ligation cover and the bracket base. This is particularly advantageous when replacing one or more interchangeable ligation covers while leaving the bracket bases still bonded or otherwise attached to the teeth. In addition, it maximizes the visible surface area available for application of decorative images, graphics, figures, patterns, designs, or other decorations to the front labial-buccal surface of the ligation cover, while still providing a small, low profile bracket. Maximizing this surface area is advantageous as the brackets are already very small such that the maximized cover surface makes any applied decoration more easily visible, distinguishable, and/or recognizable.

Any ligation cover and/or an insert as in FIGS. 5A-5B may advantageously be impregnated and/or coated with a medicament (e.g., fluoride). Such an embodiment may allow the practitioner to replace a ligation cover and/or an insert with a new ligation cover or insert once the medicament within the first ligation cover has been depleted. Such a replacement can be performed quickly and easily with little discomfort to the patient as removal and rebonding of the bracket base is not required. Administration of fluoride may be particularly advantageous during orthodontic treatment involving the use of brackets as it can be quite difficult for a patient to maintain clean teeth (particularly those portions of the teeth near the brackets) during the orthodontic treatment. Administration of fluoride may at least partially offset any tendency for increased tooth decay during such treatment.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket comprising:
   a bracket base having at least one arch wire slot formed therein, the arch wire slot being adapted to receive an arch wire therein;
   a ligation cover that is selectively slidable relative to the bracket base between an open, non-ligating position relative to the at least one arch wire slot and a closed, ligating position relative to the at least one arch wire slot; and
   a sliding mechanism that is configured to provide a sliding connection between the ligation cover and the bracket base and retain the ligation cover on the bracket base while in the open, non-ligating position,
   wherein an exterior labial surface formed by the base and ligation cover when in the closed, ligating position comprises a compound two axis curvature so that substantially all of the exterior labial surface provides a smooth, substantially continuous exterior surface that is free of discontinuities and crevices except for a single tool-receiving recess formed in the labial surface for use in selectively moving the ligation cover between the open and closed positions.

2. An orthodontic bracket as recited in claim 1, wherein the bracket consists of only two separate pieces.

3. An orthodontic bracket as recited in claim 1, further comprising latch means for holding the ligation cover in an open position when the ligation cover is open.

4. An orthodontic bracket as recited in claim 3, wherein the latch means for holding the ligation cover in an open position comprises a well formed in one of the bracket base or ligation cover and a protrusion formed on the other of the bracket base or ligation cover, the protrusion being sized to engage within the well so as to define a latched position in which the ligation cover is held open.

5. An orthodontic bracket as recited in claim 1, further comprising latch means for holding the ligation cover in an open position when the ligation cover is open and for holding the ligation cover in a closed position when the ligation cover is closed.

6. An orthodontic bracket as recited in claim 5, wherein the latch means for holding the ligation cover in an open position when open and a closed position when closed comprises:
   a groove with a first well at one end of the groove and a second well at an opposite end of the groove, the groove and wells being formed in one of the bracket base or ligation cover; and
   a protrusion formed on the other of the bracket base or ligation cover, the protrusion being sized to selectively engage within a selected well, the first well defining a latched position in which the ligation cover is held open when the protrusion is engaged therein and the second well defining a latched position in which the ligation cover is held closed when the protrusion is engaged therein.

7. An orthodontic bracket as recited in claim 1, wherein the sliding mechanism comprises a raised track and one or more rails formed on the base, the track and rails engaging within a recess formed in the ligation cover such that the track and rails guide movement of the cover as the cover is slid from an open position to a closed position.

8. An orthodontic bracket as recited in claim 1, wherein the bracket base further comprises an interchangeable aesthetic insert.

9. An orthodontic bracket as recited in claim 8, wherein the interchangeable aesthetic insert and/or the ligation cover is impregnated with a medicament.

10. An orthodontic bracket as recited in claim 1, wherein the bracket base is formed from at least one material selected from the group consisting of metal, ceramic, a polymeric resin, and glass.

11. An orthodontic bracket as recited in claim 1, wherein the ligation cover is formed from at least one material selected from the group consisting of metal, ceramic, a polymeric resin, and glass.

12. An orthodontic bracket as recited in claim 1, wherein the exterior labial surface formed by the ligation cover and/or the bracket base includes a decorative image, graphic, figure, pattern, design, or other decoration that contrasts with a surrounding surface.

13. An orthodontic bracket as recited in claim 1, wherein the bracket base further comprises a supporting ledge for supporting a leading edge of the ligation cover when closed.

14. An orthodontic bracket as recited in claim 1, wherein the ligation cover comprises two co-linear oppositely disposed ligation covers, each cover being selectively slidable towards the other ligation cover along an axis defined by the sliding mechanism.

15. An orthodontic bracket as recited in claim 14, wherein each ligation cover includes a leading edge that is cantilevered over the arch wire slot when the covers are in a closed, ligating position.

16. An orthodontic bracket as recited in claim 1, wherein the exterior labial surface of the bracket defines a substantially rectangular shape with rounded corners.

17. An orthodontic bracket as recited in claim 1, wherein the exterior labial surface of the bracket defines a substantially teardrop shape with rounded corners.

18. An orthodontic bracket comprising:
   a bracket base having at least one arch wire slot formed therein, the arch wire slot being adapted to receive an arch wire therein;
   a ligation cover that is selectively slidable relative to the bracket base between an open, non-ligating position relative to the at least one arch wire slot and a closed, ligating position relative to the at least one arch wire slot; and
   a single recess formed in the bracket base or ligation cover near a longitudinal center of the bracket configured to receive an opening tool to aid in opening the ligation cover,
   wherein an exterior labial surface formed by the base and ligation cover when in the closed, ligating position comprises a compound two axis curvature so that substantially all of the exterior labial surface provides a smooth, substantially continuous exterior surface that is substantially free of discontinuities and crevices except for the single recess.

19. An orthodontic bracket as recited in claim 18, wherein the recess is formed at an incisal edge of a labially exposed portion of the bracket base.

20. An orthodontic bracket as recited in claim 18, wherein the recess is formed at a gingival edge of a labially exposed portion of the ligation cover.

21. An orthodontic bracket comprising:
   a bracket base having at least one arch wire slot formed therein, the arch wire slot being adapted to receive an arch wire therein;
   a ligation cover that is selectively slidable relative to the bracket base between an open, non-ligating position relative to the at least one arch wire slot and a closed, ligating position relative to the at least one arch wire slot; and
   a sliding mechanism comprising a raised track and one or more rails formed on the base, the track and rails engaging within a corresponding recess formed in a side of the ligation cover such that the track and rails guide movement of the cover as the cover is slid from an open position to a closed position,
   wherein an exterior labial surface formed by the base and ligation cover when in the closed, ligating position comprises a compound two axis curvature so that substantially all of the exterior labial surface provides a smooth, substantially continuous exterior surface that is substantially free of discontinuities and crevices.

22. An orthodontic bracket comprising:
   a bracket base having at least one arch wire slot formed therein, the arch wire slot being adapted to receive an arch wire therein;

a ligation cover that is selectively slidable relative to the bracket base between an open, non-ligating position relative to the at least one arch wire slot and a closed, ligating position relative to the at least one arch wire slot; and a sliding mechanism comprising a raised track and one or more rails extending laterally from the raised track formed on an upper surface of said bracket base, the track and the one or more rails engaging within a corresponding recess formed in an interior region in a lower surface of the ligation cover such that the track and the one or more rails guide movement of the cover as the cover is slid from an open position to a closed position, and wherein the ligation cover encloses a pair of opposing mesial-distal sides of the raised track and the one or more rails within the interior region of the ligation cover when in the closed position.

23. An orthodontic bracket as recited in claim 22, wherein the ligation cover includes a pair of opposing mesial-distal walls that slidably contact a labial surface of a tooth-bonding pad of the bracket base when the ligation cover is moved into the closed position.

24. An orthodontic bracket as recited in claim 22, wherein the raised track includes an end surface that at least partially defines the at least one arch wire slot.

25. An orthodontic bracket as recited in claim 24, wherein the ligation cover includes at least one wall that lies adjacent to and is substantially co-planar with the end surface of the raised track so as to further define the at least one arch wire slot when the ligation cover is in the closed position.

26. An orthodontic bracket as recited in claim 22, further comprising a recess formed in a labial surface of the bracket base configured to receive a tool to aid in opening the ligation cover.

27. An orthodontic bracket as recited in claim 22, further comprising a recess formed in a labial surface of the ligation cover configured to receive a tool to aid in opening the ligation cover.

28. An orthodontic bracket as recited in claim 22, wherein the bracket base further comprises a supporting ledge for supporting a leading edge of the ligation cover when in the closed position.

29. An orthodontic bracket as recited in claim 22, wherein the bracket base further comprises a recess that partially encloses and overlaps a labial surface of a leading edge of the ligation cover when in the closed position.

30. An orthodontic bracket as recited in claim 22, wherein an exterior labial bracket surface formed when the ligation cover is in the closed position comprises a compound two axis curvature and provides a smooth, substantially continuous exterior surface except for a single tool-receiving recess.

\* \* \* \* \*

UNITED STATES PATENT AND TRADEMARK OFFICE
CERTIFICATE OF CORRECTION

PATENT NO. : 7,963,767 B2
APPLICATION NO. : 12/146608
DATED : June 21, 2011
INVENTOR(S) : Lewis et al.

It is certified that error appears in the above-identified patent and that said Letters Patent is hereby corrected as shown below:

Column 3
Line 62, change "an" to --a--

Column 4
Line 17, change "a" to --an--
Line 30, change "a" to --an--

Column 8
Line 17, change "practitioner" to --practitioner.--

Column 11
Line 39, change "501" to --601--

Column 13
Line 53, change "disclose" to --disclosure--

Signed and Sealed this
Twenty-seventh Day of September, 2011

David J. Kappos
*Director of the United States Patent and Trademark Office*